US006969702B2

(12) United States Patent
Bertilsson et al.

(10) Patent No.: US 6,969,702 B2
(45) Date of Patent: Nov. 29, 2005

(54) COMPOUNDS AND METHODS FOR INCREASING NEUROGENESIS

(75) Inventors: Göran Bertilsson, Västerhaninge (SE); Rikard Erlandsson, Sundyberg (SE); Jonas Frisen, Stockholm (SE); Anders Haegerstrand, Danderyd (SE); Jessica Heidrich, Årsta (SE); Nina Hellström, Södertälje (SE); Johan Häggblad, Västgötagränd (SE); Katarina Jansson, Johanneshov (SE); Jarkko Kortesmaa, Stockholm (SE); Per Lindquist, Bromma (SE); Hanna Lundh, Solna (SE); Jacqueline McGuire, Stockholm (SE); Alex Mercer, Bromma (SE); Karl Nyberg, Uppsala (SE); Amina Ossoinak, Stockholm (SE); Cesare Patrone, Hägersten (SE); Harriet Rönnholm, Trångsund (SE); Lilian Wikström, Spånga (SE); Olof Zachrisson, Spånga (SE)

(73) Assignee: NeuroNova AB, Stockholm (SE)

( * ) Notice: Subject to any disclaimer, the term of this patent is extended or adjusted under 35 U.S.C. 154(b) by 116 days.

(21) Appl. No.: 10/850,055

(22) Filed: May 19, 2004

(65) Prior Publication Data

US 2005/0009742 A1 Jan. 13, 2005

Related U.S. Application Data

(63) Continuation-in-part of application No. 10/718,071, filed on Nov. 20, 2003.
(60) Provisional application No. 60/427,912, filed on Nov. 20, 2002.

(51) Int. Cl.[7] .................. A61N 37/18; A61K 38/00
(52) U.S. Cl. .................. 514/12; 530/307; 530/324
(58) Field of Search ................ 514/12; 530/307, 530/324

(56) References Cited

U.S. PATENT DOCUMENTS

5,665,380 A * 9/1997 Wallach et al. ............. 424/450

FOREIGN PATENT DOCUMENTS

| WO | WO 00/12099 | 3/2000 |
| WO | WO 01/85981 | 11/2001 |

OTHER PUBLICATIONS

Jackowski, "Neural injury repair: hope for the future as barriers to effective CNS regeneration become clearer," British Journal of Neurosurgery, (1995), 9, p. 303–317.*
Asanuma et al. (1996). Mol. Brain Res. 41: 210–215.
Cameron and McKay (1998). Current Opinion in Neurobiol. 8: 677–680.
Cassidy and Frisen (2001). Nature 412: 690–691.
Dinter et al. (1997). J. Mol. Med. 75: 95–102.
D'Sa and Duman (2002). Bipolar Disorders 4: 183–194.
Duman et al. (2001). J. Pharmacol. and Ex. Therapeutics 299: 401–407.
Duman et al. (2001). Neuropsychopharmacol. 25: 836–844.
Duprat et al. (2000). Mol. Pharmacol. 57: 906–912.
Hallbergson et al. (2003). J. Clinical Investigation 112: 1128–1133.
Hartikka et al. (1992). J. Neuroscience Res. 32: 190–201.
Iona et al. (1998). Mol. Pharmacol. 53: 23–32.
Kim et al. (2000). Society for Neuroscience 26: 2316, Abstract No. 868.2.
Malberg et al. (2000). J. Neuroscience 20: 9104–9110.
Maric et al. (2000). Cerebral Cortex 10: 561–573.
Nakagawa et al. (2002). J. Neuroscience 22: 3673–3682.
Nash and Brotchle (2000). J. Neuroscience 20: 7782–7789.
Pahan et al. (1997). J. Biol. Chem. 272: 7786–7791.
Palmer (1985). Life Sciences 36: 1995–2006.
Sakaki et al. (1997). J. Neurobiology 32: 62–68.
Sugioka et al.(1996). J. Physiology 493: 855–863.
Sugioka et al. (1999). Int. J. Devl. Neuroscience 17: 163–172.
Temple (2001). Nature 414: 112–117.
Vitolo et al. (2002). Proc. Natl. Acad. Sci. USA 99: 13217–13221.
Wyttenbach et al. (2001). Human Mol. Genetics 10: 1829–1845.
Yamashita et al. (1994). J. Neurobiology 25: 1144–1153.
Yamashita and Sugioka (1998). News Physiol. Sci. 13: 75–79.

* cited by examiner

Primary Examiner—Karen Cochrane Carlson
Assistant Examiner—Agnes Rooke
(74) Attorney, Agent, or Firm—Mintz Levin Cohn Ferris Clovsky and Popeo PC

(57) ABSTRACT

The invention is directed to methods of promoting neurogenesis by contacting neuronal tissue with neurogenesis increasing agents. Novel methods for treating neurological disorders using neurogenesis increasing agents are disclosed.

16 Claims, 3 Drawing Sheets

A. PACAP

Mouse

Human

B. Cholera toxin

Mouse

Human

SEQUENCE LISTING

```
<160> NUMBER OF SEQ ID NOS: 66

<210> SEQ ID NO 1
<211> LENGTH: 32
<212> TYPE: PRT
<213> ORGANISM: salmon

<400> SEQUENCE: 1

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 2
<211> LENGTH: 32
<212> TYPE: PRT
<213> ORGANISM: Homo sapiens

<400> SEQUENCE: 2

Cys Gly Asn Leu Ser Thr Cys Met Leu Gly Thr Tyr Thr Gln Asp Phe
1               5                   10                  15
```

-continued

```
Asn Lys Phe His Thr Phe Pro Gln Thr Ala Ile Gly Val Gly Ala Pro
            20                  25                  30

<210> SEQ ID NO 3
<211> LENGTH: 39
<212> TYPE: PRT
<213> ORGANISM: Homo sapines

<400> SEQUENCE: 3

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 4
<211> LENGTH: 39
<212> TYPE: PRT
<213> ORGANISM: Homo sapiens

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 25
<212> TYPE: PRT
<213> ORGANISM: salmon

<400> SEQUENCE: 5

Val Leu Gly Lys Leu Ser Gln Glu Leu His Lys Leu Gln Thr Tyr Pro
1               5                   10                  15

Arg Thr Asn Thr Gly Ser Gly Thr Pro
            20                  25

<210> SEQ ID NO 6
<211> LENGTH: 30
<212> TYPE: PRT
<213> ORGANISM: Homo sapiens

<400> SEQUENCE: 6

Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala Phe
            20                  25                  30

<210> SEQ ID NO 7
<211> LENGTH: 37
<212> TYPE: PRT
<213> ORGANISM: Homo sapiens

<400> SEQUENCE: 7

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30
```

Gly Ser Asn Thr Tyr
        35

<210> SEQ ID NO 8
<211> LENGTH: 21
<212> TYPE: PRT
<213> ORGANISM: Homo sapiens

<400> SEQUENCE: 8

Asp Met Ser Ser Asp Leu Glu Arg Asp His Arg Pro His Val Ser Met
1               5                   10                  15

Pro Gln Asn Ala Asn
            20

<210> SEQ ID NO 9
<211> LENGTH: 37
<212> TYPE: PRT
<213> ORGANISM: Homo sapiens

<400> SEQUENCE: 9

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 10
<211> LENGTH: 38
<212> TYPE: PRT
<213> ORGANISM: Homo sapiens

<400> SEQUENCE: 10

Ser Cys Asn Thr Ala Thr Cys Met Thr His Arg Leu Val Gly Leu Leu
1               5                   10                  15

Ser Arg Ser Gly Ser Met Val Arg Ser Asn Leu Leu Pro Thr Lys Met
            20                  25                  30

Gly Phe Lys Val Phe Gly
        35

<210> SEQ ID NO 11
<211> LENGTH: 37
<212> TYPE: PRT
<213> ORGANISM: Homo sapiens

<400> SEQUENCE: 11

Ser Cys Asn Thr Ala Ser Cys Val Thr His Lys Met Thr Gly Trp Leu
1               5                   10                  15

Ser Arg Ser Gly Ser Val Ala Lys Asn Asn Phe Met Pro Thr Asn Val
            20                  25                  30

Asp Ser Lys Ile Leu
        35

<210> SEQ ID NO 12
<211> LENGTH: 37
<212> TYPE: PRT
<213> ORGANISM: Homo sapiens

<400> SEQUENCE: 12

Ser Cys Asn Thr Ala Ile Cys Val Thr His Lys Met Ala Gly Trp Leu
1               5                   10                  15

-continued

Ser Arg Ser Gly Ser Val Val Lys Asn Asn Phe Met Pro Ile Asn Met
            20                  25                  30

Gly Ser Lys Val Leu
        35

<210> SEQ ID NO 13
<211> LENGTH: 27
<212> TYPE: PRT
<213> ORGANISM: Homo sapiens

<400> SEQUENCE: 13

His Ala Asp Gly Val Phe Thr Ser Asp Phe Ser Lys Leu Leu Gly Gln
1               5                   10                  15

Leu Ser Ala Lys Lys Tyr Leu Glu Ser Leu Met
            20                  25

<210> SEQ ID NO 14
<211> LENGTH: 47
<212> TYPE: PRT
<213> ORGANISM: Homo sapiens

<400> SEQUENCE: 14

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 15
<211> LENGTH: 32
<212> TYPE: PRT
<213> ORGANISM: salmon

<400> SEQUENCE: 15

Cys Ser Asn Leu Ser Thr Cys Val Leu Gly Lys Leu Ser Gln Asp Leu
1               5                   10                  15

Asp Lys Leu Gln Lys Phe Pro Arg Thr Asn Thr Gly Ala Gly Val Pro
            20                  25                  30

<210> SEQ ID NO 16
<211> LENGTH: 32
<212> TYPE: PRT
<213> ORGANISM: salmon
<220> FEATURE:
<221> NAME/KEY: misc_feature
<222> LOCATION: (21)..(21)
<223> OTHER INFORMATION: ornithine

<400> SEQUENCE: 16

Cys Ser Asn Leu Ser Thr Cys Val Leu Gly Lys Leu Ser Gln Asp Leu
1               5                   10                  15

Asp Lys Leu Gln Xaa Phe Pro Arg Thr Asn Thr Gly Ala Gly Val Pro
            20                  25                  30

<210> SEQ ID NO 17
<211> LENGTH: 24
<212> TYPE: PRT
<213> ORGANISM: salmon

<400> SEQUENCE: 17

Leu Gly Lys Leu Ser Gln Asp Leu His Arg Leu Gln Thr Phe Pro Arg

-continued

```
                 1               5                  10                 15
Thr Asn Thr Gly Ala Asn Val Tyr
                20

<210> SEQ ID NO 18
<211> LENGTH: 32
<212> TYPE: PRT
<213> ORGANISM: salmon

<400> SEQUENCE: 18

Cys Ser Asn Leu Ser Thr Cys Val Leu Gly Arg Leu Ser Lys Asp Leu
 1               5                  10                  15

His Arg Leu Gln Thr Phe Pro Arg Thr Asn Thr Gly Ala Gly Val Pro
            20                  25                  30

<210> SEQ ID NO 19
<211> LENGTH: 32
<212> TYPE: PRT
<213> ORGANISM: Homo sapiens

<400> SEQUENCE: 19

Cys Ser Asn Leu Ser Thr Cys Val Leu Gly Lys Leu Ser Gln Asp Leu
 1               5                  10                  15

His Lys Leu Gln Thr Phe Pro Arg Thr Asn Thr Gly Ala Gly Val Pro
            20                  25                  30

<210> SEQ ID NO 20
<211> LENGTH: 32
<212> TYPE: PRT
<213> ORGANISM: eel
<220> FEATURE:
<221> NAME/KEY: misc_feature
<222> LOCATION: (1)..(1)
<223> OTHER INFORMATION: aminosuberic acid
<220> FEATURE:
<221> NAME/KEY: misc_feature
<222> LOCATION: (7)..(7)
<223> OTHER INFORMATION: aminosuberic acid

<400> SEQUENCE: 20

Xaa Ser Asn Leu Ser Thr Xaa Val Leu Gly Lys Leu Ser Gln Glu Leu
 1               5                  10                  15

His Lys Leu Gln Thr Tyr Pro Arg Thr Asp Val Gly Ala Gly Thr Pro
            20                  25                  30

<210> SEQ ID NO 21
<211> LENGTH: 39
<212> TYPE: PRT
<213> ORGANISM: Homo sapiens

<400> SEQUENCE: 21

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 22
<211> LENGTH: 37
<212> TYPE: PRT
<213> ORGANISM: Homo sapiens

<400> SEQUENCE: 22
```

His Asp Glu Phe Glu Arg His Ala Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
            35

<210> SEQ ID NO 23
<211> LENGTH: 15
<212> TYPE: PRT
<213> ORGANISM: Homo sapiens

<400> SEQUENCE: 23

His Gly Glu Gly Thr Phe Thr Ser Asp Leu Ser Lys Met Glu Glu
1               5                   10                  15

<210> SEQ ID NO 24
<211> LENGTH: 16
<212> TYPE: PRT
<213> ORGANISM: Homo sapiens

<400> SEQUENCE: 24

His Gly Glu Gly Thr Phe Thr Ser Asp Leu Ser Lys Met Glu Glu Glu
1               5                   10                  15

<210> SEQ ID NO 25
<211> LENGTH: 15
<212> TYPE: PRT
<213> ORGANISM: Homo sapiens

<400> SEQUENCE: 25

His Ser Glu Gly Thr Phe Thr Ser Asp Leu Ser Lys Met Glu Glu
1               5                   10                  15

<210> SEQ ID NO 26
<211> LENGTH: 15
<212> TYPE: PRT
<213> ORGANISM: Homo sapiens

<400> SEQUENCE: 26

His Ala Glu Gly Thr Phe Thr Ser Asp Leu Ser Lys Met Glu Glu
1               5                   10                  15

<210> SEQ ID NO 27
<211> LENGTH: 9
<212> TYPE: PRT
<213> ORGANISM: Homo sapiens

<400> SEQUENCE: 27

His Gly Glu Gly Thr Phe Thr Ser Asp
1               5

<210> SEQ ID NO 28
<211> LENGTH: 31
<212> TYPE: PRT
<213> ORGANISM: Homo sapiens

<400> SEQUENCE: 28

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

```
<210> SEQ ID NO 29
<211> LENGTH: 37
<212> TYPE: PRT
<213> ORGANISM: Homo sapiens

<400> SEQUENCE: 29

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 30
<211> LENGTH: 11
<212> TYPE: PRT
<213> ORGANISM: Homo sapiens

<400> SEQUENCE: 30

His Ala Glu Gly Thr Phe Thr Ser Asp Val Ser
1               5                   10

<210> SEQ ID NO 31
<211> LENGTH: 31
<212> TYPE: PRT
<213> ORGANISM: Homo sapiens

<400> SEQUENCE: 31

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 32
<211> LENGTH: 31
<212> TYPE: PRT
<213> ORGANISM: Homo sapiens

<400> SEQUENCE: 32

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Lys
            20                  25                  30

<210> SEQ ID NO 33
<211> LENGTH: 31
<212> TYPE: PRT
<213> ORGANISM: Homo sapiens

<400> SEQUENCE: 33

His Ala Glu Gly Thr Phe Thr Ser Asp Val Ser Ser Tyr Leu Glu Gly
1               5                   10                  15

Gln Ala Ala Lys Glu Phe Ile Ala Trp Lys Val Arg Gly Arg Gly
            20                  25                  30

<210> SEQ ID NO 34
<211> LENGTH: 37
<212> TYPE: PRT
<213> ORGANISM: Homo sapiens

<400> SEQUENCE: 34

Lys Cys Asn Thr Ala Thr Cys Ala Thr Gln Arg Leu Ala Asn Phe Leu
```

```
                1               5                  10                 15
        Val His Ser Ser Asn Asn Phe Gly Pro Ile Leu Pro Pro Tyr Asn Val
                        20                  25                  30

Gly Ser Asn Thr Tyr
                    35

<210> SEQ ID NO 35
        <211> LENGTH: 37
        <212> TYPE: PRT
        <213> ORGANISM: Homo sapiens

<400> SEQUENCE: 35

Lys Cys Asn Thr Ala Thr Cys Ala Thr Gln Arg Leu Ala Asn Phe Leu
        1               5                   10                  15
        Val His Ser Ser Asn Asn Phe Gly Ala Ile Leu Ser Ser Thr Asn Val
                        20                  25                  30

Gly Ser Asn Thr Tyr
                    35

<210> SEQ ID NO 36
        <211> LENGTH: 9
        <212> TYPE: PRT
        <213> ORGANISM: Homo sapiens

<400> SEQUENCE: 36

His Ser Glu Gly Thr Phe Thr Ser Asp
        1               5

<210> SEQ ID NO 37
        <211> LENGTH: 15
        <212> TYPE: PRT
        <213> ORGANISM: Homo sapiens

<400> SEQUENCE: 37

His Ser Thr Gly Thr Phe Thr Ser Met Asp Thr Ser Gln Leu Pro
        1               5                   10                  15

<210> SEQ ID NO 38
        <211> LENGTH: 11
        <212> TYPE: PRT
        <213> ORGANISM: Homo sapiens

<400> SEQUENCE: 38

His Ser Thr Gly Thr Phe Thr Ser Met Asp Thr
        1               5                   10

<210> SEQ ID NO 39
        <211> LENGTH: 10
        <212> TYPE: PRT
        <213> ORGANISM: Homo sapiens

<400> SEQUENCE: 39

His Ser Thr Gly Thr Phe Thr Ser Met Asp
        1               5                   10

<210> SEQ ID NO 40
        <211> LENGTH: 10
        <212> TYPE: PRT
        <213> ORGANISM: Homo sapiens

<400> SEQUENCE: 40

Gln Ser Thr Gly Thr Phe Thr Ser Met Asp
        1               5                   10
```

<210> SEQ ID NO 41
<211> LENGTH: 10
<212> TYPE: PRT
<213> ORGANISM: Homo sapiens

<400> SEQUENCE: 41

Gln Thr Thr Gly Thr Phe Thr Ser Met Asp
1               5                   10

<210> SEQ ID NO 42
<211> LENGTH: 10
<212> TYPE: PRT
<213> ORGANISM: Homo sapiens

<400> SEQUENCE: 42

His Thr Thr Gly Thr Phe Thr Ser Met Asp
1               5                   10

<210> SEQ ID NO 43
<211> LENGTH: 19
<212> TYPE: DNA
<213> ORGANISM: Artificial
<220> FEATURE:
<223> OTHER INFORMATION: Primer

<400> SEQUENCE: 43
caatgtgctg gtgtgctgg                                              19

<210> SEQ ID NO 44
<211> LENGTH: 20
<212> TYPE: DNA
<213> ORGANISM: Primer

<400> SEQUENCE: 44
gacgagtacg acccacagat                                             20

<210> SEQ ID NO 45
<211> LENGTH: 19
<212> TYPE: DNA
<213> ORGANISM: Artificial
<220> FEATURE:
<223> OTHER INFORMATION: Primer

<400> SEQUENCE: 45
caggatcatt taccagaac                                              19

<210> SEQ ID NO 46
<211> LENGTH: 19
<212> TYPE: DNA
<213> ORGANISM: Artificial
<220> FEATURE:
<223> OTHER INFORMATION: Primer

<400> SEQUENCE: 46
cttgtagaat tcgtcgcag                                              19

<210> SEQ ID NO 47
<211> LENGTH: 20
<212> TYPE: DNA
<213> ORGANISM: Artificial
<220> FEATURE:
<223> OTHER INFORMATION: Primer

<400> SEQUENCE: 47

-continued agagcctaag ttgccaaagg                          20

<210> SEQ ID NO 48
<211> LENGTH: 20
<212> TYPE: DNA
<213> ORGANISM: Artificial
<220> FEATURE:
<223> OTHER INFORMATION: Primer

<400> SEQUENCE: 48
gtaacttaaa cacgactaag                          20

<210> SEQ ID NO 49
<211> LENGTH: 18
<212> TYPE: DNA
<213> ORGANISM: Artificial
<220> FEATURE:
<223> OTHER INFORMATION: Primer

<400> SEQUENCE: 49
gaaccggaac ctgcactc                            18

<210> SEQ ID NO 50
<211> LENGTH: 19
<212> TYPE: DNA
<213> ORGANISM: Artificial
<220> FEATURE:
<223> OTHER INFORMATION: Primer

<400> SEQUENCE: 50
gagtggtagg acgacccgt                           19

<210> SEQ ID NO 51
<211> LENGTH: 20
<212> TYPE: DNA
<213> ORGANISM: Artificial
<220> FEATURE:
<223> OTHER INFORMATION: Primer

<400> SEQUENCE: 51
gagaacatct tggtcatagg                          20

<210> SEQ ID NO 52
<211> LENGTH: 20
<212> TYPE: DNA
<213> ORGANISM: Artificial
<220> FEATURE:
<223> OTHER INFORMATION: Primer

<400> SEQUENCE: 52
gaagtagagt gaaattacga                          20

<210> SEQ ID NO 53
<211> LENGTH: 19
<212> TYPE: DNA
<213> ORGANISM: Artificial
<220> FEATURE:
<223> OTHER INFORMATION: Primer

<400> SEQUENCE: 53
gctacaccat tggctacgg                           19

<210> SEQ ID NO 54
<211> LENGTH: 20
<212> TYPE: DNA
<213> ORGANISM: Artificial

```
<220> FEATURE:
<223> OTHER INFORMATION: Primer

<400> SEQUENCE: 54
gtccttctca ctgtcgtcag                                           20

<210> SEQ ID NO 55
<211> LENGTH: 21
<212> TYPE: DNA
<213> ORGANISM: Artificial
<220> FEATURE:
<223> OTHER INFORMATION: Primer

<400> SEQUENCE: 55
gatgtctctt gcaacaggaa g                                         21

<210> SEQ ID NO 56
<211> LENGTH: 20
<212> TYPE: DNA
<213> ORGANISM: Artificial
<220> FEATURE:
<223> OTHER INFORMATION: Primer

<400> SEQUENCE: 56
caggtgatgt accacaaacg                                           20

<210> SEQ ID NO 57
<211> LENGTH: 25
<212> TYPE: DNA
<213> ORGANISM: Artificial
<220> FEATURE:
<223> OTHER INFORMATION: Primer

<400> SEQUENCE: 57
gggaactcta tggtcatcta cgtga                                     25

<210> SEQ ID NO 58
<211> LENGTH: 23
<212> TYPE: DNA
<213> ORGANISM: Artificial
<220> FEATURE:
<223> OTHER INFORMATION: Primer

<400> SEQUENCE: 58
cccgaagcac aacatgtgta aag                                       23

<210> SEQ ID NO 59
<211> LENGTH: 25
<212> TYPE: DNA
<213> ORGANISM: Artificial
<220> FEATURE:
<223> OTHER INFORMATION: Primer

<400> SEQUENCE: 59
ggcaacacac ttgtcattta tgtca                                     25

<210> SEQ ID NO 60
<211> LENGTH: 25
<212> TYPE: DNA
<213> ORGANISM: Artificial
<220> FEATURE:
<223> OTHER INFORMATION: Primer

<400> SEQUENCE: 60
agtggtagta gacagaaacg atgga                                     25
```

-continued

```
<210> SEQ ID NO 61
<211> LENGTH: 22
<212> TYPE: DNA
<213> ORGANISM: Artificial
<220> FEATURE:
<223> OTHER INFORMATION: Primer

<400> SEQUENCE: 61
tactttgatg acacaggctg ct                                             22

<210> SEQ ID NO 62
<211> LENGTH: 22
<212> TYPE: DNA
<213> ORGANISM: Artificial
<220> FEATURE:
<223> OTHER INFORMATION: Primer

<400> SEQUENCE: 62
tcccgaaaca ccaccgacat ga                                             22

<210> SEQ ID NO 63
<211> LENGTH: 24
<212> TYPE: DNA
<213> ORGANISM: Artificial
<220> FEATURE:
<223> OTHER INFORMATION: Primer

<400> SEQUENCE: 63
aactgcaaaa tgcgtacgtt cttt                                           24

<210> SEQ ID NO 64
<211> LENGTH: 25
<212> TYPE: DNA
<213> ORGANISM: Artificial
<220> FEATURE:
<223> OTHER INFORMATION: Primer

<400> SEQUENCE: 64
tacagaacgt tgatgaagac ctacg                                          25

<210> SEQ ID NO 65
<211> LENGTH: 22
<212> TYPE: DNA
<213> ORGANISM: Artificial
<220> FEATURE:
<223> OTHER INFORMATION: Primer

<400> SEQUENCE: 65
gtaccacggt gtccctctca ga                                             22

<210> SEQ ID NO 66
<211> LENGTH: 20
<212> TYPE: DNA
<213> ORGANISM: Artificial
<220> FEATURE:
<223> OTHER INFORMATION: Primer

<400> SEQUENCE: 66
tgcgtgaaag aaagaggcgg                                                20
```

COMPOUNDS AND METHODS FOR INCREASING NEUROGENESIS

RELATED APPLICATIONS

This application is a continuation in part of U.S. Ser. No. 10/718,071, filed Nov. 20, 2003, which claims benefit of U.S. Ser. No. 60/427,912, filed Nov. 20, 2002.

FIELD OF THE INVENTION

The invention is directed to in vitro and in vivo methods of modulating neurogenesis. Novel agents for increasing intracellular levels of cAMP, $Ca^{2+}$ and for modulating neurogenesis are also provided.

BACKGROUND OF THE INVENTION

Neural stem cells (NSC) are a source for new neurons in the mammalian CNS. NSC are located within the ependymal and/or subventricular zone (SVZ) lining the lateral ventricle (Doetsch et al., 1999; Johansson et al., 1999b) and in the dentate gyrus of the hippocampal formation (Gage et al., 1998). Studies have revealed the potential for several additional locations of NSC within the adult CNS (Palmer et al., 1999). Asymmetric division of NSC maintains their starting number, while generating a population of rapidly dividing precursor, or progenitor cells (Johansson et al., 1999b). The progenitor cells respond to a range of cues that dictate the extent of their proliferation and their fate, both in terms of differentiation and positioning.

The NSC of the ventricular system in the adult are likely counterparts of the embryonic ventricular zone stem cells lining the neural tube. The progeny of these embryonic cells migrate away to form the CNS as differentiated neurons and glia (Jacobson, 1991). NSC persist in the adult lateral ventricle wall (LVW), generating neuronal progenitors that migrate down the rostral migratory stream to the olfactory bulb. There, they differentiate into granule cells and periglomerular neurons (Lois and Alvarez-Buylla, 1993). Substantial neuronal death occurs in the olfactory bulb, creating a need for continuous replacement of lost neurons which is satisfied by the migrating progenitors derived from the LVW (Biebl et al., 2000). In addition, there are indications that lost neurons from other brain regions can be replaced by progenitors from the LVW that differentiate into the phenotype of the lost neurons with appropriate neuronal projections and synapses with the correct target cell type (Snyder et al., 1997; Magavi et al., 2000).

In vitro cultivation techniques have been established to identify the external signals involved in the regulation of NSC proliferation and differentiation (Johansson et al., 1999b; Johansson et al., 1999a). The mitogens EGF and basic FGF allow cell culture expansion of neural progenitors isolated from the ventricle wall and the hippocampus (McKay, 1997; Johansson et al., 1999a). These dividing progenitors remain in an undifferentiated state, and grow into large clones of cells known as neurospheres. Upon the withdrawal of the mitogens and the addition of serum, the progenitors differentiate into neurons, astrocytes and oligodendrocytes, which are the three cell lineages of the brain (Doetsch et al., 1999; Johansson et al., 1999b). Specific growth factors can be added to alter the proportions of each cell type formed. For example, CNTF acts to direct the neural progenitors to an astrocytic fate (Johe et al., 1996; Rajan and McKay, 1998). The thyroid hormone, triiodothyronine (T3), promotes oligodendrocyte differentiation (Johe et al., 1996), while PDGF enhances neuronal differentiation by progenitor cells (Johe et al., 1996; Williams et al., 1997). Recently, it has been shown that indeed adult regenerated neurons are integrated into the existing brain circuitry, and contribute to ameliorating neurological deficits (Nakatomi et al., 2002). Interestingly, observations have also shown that neurogenesis is occurring not only at the level of the olfactory bulb and hippocampus. In this respect it has been suggested by Zhao et al. that this process can also occur in the adult mouse substantia nigra, opening up a new field of investigation for the treatment of Parkinson's disease (Zhao et al., 2003).

The ability to expand neural progenitors and manipulate their cell fate has enormous implications for transplant therapies for neurological diseases where specific cell types are lost. Parkinson's disease (PD), for example, is characterized by degeneration of dopaminergic neurons in the substantia nigra. Previous transplantation treatments for PD patients have used fetal tissue taken from the ventral midbrain at a time when substantia nigra dopaminergic neurons are undergoing terminal differentiation (Herman and Abrous, 1994). These cells have been grafted onto the striatum where they form synaptic contacts with host striatal neurons, their normal synaptic target. This restores dopamine turnover and release to normal levels with significant functional benefits to the patient (Herman and Abrous, 1994) (for review see Bjorklund and Lindvall, 2000). However, the grafting of fetal tissue is limited by ethical considerations and a lack of donor tissue. The expansion and manipulation of adult NSC can potentially provide a range of well characterized cells for transplant-based strategies for neurodegenerative disease such as PD. To this aim, the identification of factors and pathways that govern the proliferation and differentiation of neural cell types is fundamentally important.

Studies have shown that intraventricular infusion of both EGF and basic FGF induces proliferation in the adult ventricle wall cell population. In the case of EGF, extensive migration of progenitors into the neighboring striatal parenchyma has been observed (Craig et al., 1996; Kuhn et al., 1997). EGF increases differentiation into glial lineage and reduced the generation of neurons (Kuhn et al., 1997). Additionally, intraventricular infusion of BDNF in adult rats increases the number of newly generated neurons in the olfactory bulb and rostral migratory stream, and in parenchymal structures, including the striatum, septum, thalamus and hypothalamus (Pencea et al., 2001). Thus, several studies have shown that the proliferation of progenitors within the SVZ of the LVW can be stimulated and that their lineage can be guided to neuronal or glial fates. Yet, the number of factors known to affect neurogenesis in vivo is small and their effects are adverse or limited.

BRIEF SUMMARY OF THE INVENTION

One embodiment of the invention is directed to a method for modulating neurogenesis in neural tissue of a patient that exhibits at least one symptom of a central nervous system disorder. The disorder may be, for example, neurodegenerative disorders, ischemic disorders, neurological traumas, and learning and memory disorders. In the method, one or more neurogenesis modulating agent is administered to the patient.

The neurogenesis modulating agent may be a cAMP analog, an inhibitor of cAMP-specific phosphodiesterase, an activator of adenylate cyclase, and an activator of ADP-ribosylation of a stimulatory G protein. These neurogenesis modulating agent are listed in the Detailed Description. The disorders that may be treated by the methods of the invention are also listed in the detailed description section and include, at least, Parkinson's disease and Parkinsonian disorders, Huntington's disease, Alzheimer's disease, multiple sclerosis, amyotrophic lateral sclerosis, Shy-Drager syndrome, progressive supranuclear palsy, Lewy body disease, spinal ischemia, spinal cord injuries, ischemic stroke, cerebral infarction, spinal cord injury, and cancer-related brain and spinal cord injury, multi-infarct dementia, geriatric dementia, other cognitive impairments, and depression.

Administration may be systemic or direct into the CNS of a patient. Routes of administration include oral, subcutaneous, intraperitoneal, intramuscular, intracerebroventricular, intraparenchymal, intrathecal, intracranial, buccal, mucosal, nasal, pulmonary, and rectal administration or administration by a liposome delivery system.

Another embodiment of the invention is directed to a method of increasing cAMP levels in a cell, such as a NSC by administrating a novel cAMP elevating agent (a neurogenesis modulating agent) to the cell. In this disclosure administering an agent to a cell comprising contacting a cell with an agent. The novel cAMP elevating agent may be thyrocalcitonin (salmon), calcitonin (human), and analogs thereof, and any combination thereof. The cell may be in a patient, in which case the method is a method for stimulating intracellular cAMP in a cell of a patient. The cell may be a cell from a neural tissue. For example, the cell may be a neural stem cell or a neural progenitor cell. The method of administration and the levels of administration may be any method or level discussed for neurogenesis modulating agents in this disclosure.

This disclosure also shows a role for G-protein coupled receptors (GPCRs) and their ligands in stem cells biology in vitro and in vivo. The invention is based on our expression data (PCR and cDNA library data) and in vitro proliferation data, which shows that modulation of intracellular cAMP or $Ca^{2+}$ levels through various GPCRs can be used to influence proliferation, migration, differentiation or survival of adult neural stem cells (aNSC) and their progeny in vitro as well as in situ in the intact brain. This data also indicates CREB as a downstream link between GPCRs and transcription.

Another embodiment of the invention is directed to a method for inducing neurogenesis in vitro. In the method, a population of neural cells (comprising neural stem cells) is cultured. Then, at least one neurogenesis modulating agent is administered to the cell. The administration is repeated, if necessary, until a desired level of neurogenesis is achieved. The neural cell may be cultured from tissue such as cortex, olfactory tubercle, retina, septum, lateral ganglionic eminence, medial ganglionic eminence, amygdala, hippocampus, thalamus, hypothalamus, ventral and dorsal mesencephalon, brain stem, cerebellum, spinal cord.

Another embodiment of the invention involves the use of a neurogenesis modulating agent for the preparation of a medicament for treating a mammal exhibiting at least one symptom of a central nervous system disorder selected from the group consisting of neurodegenerative disorders, ischemic disorders, neurological traumas, and learning and memory disorders which can be improved or prevented by the administration of the neurogenesis modulating agent.

In all cases, the cell, neural tissue, or patient may be any mammal such as rat, mice, cat, dog, horse, pig, goat, cow and in particular human (adult, juvenile or fetal).

DETAILED DESCRIPTION OF THE INVENTION

Figure 1:
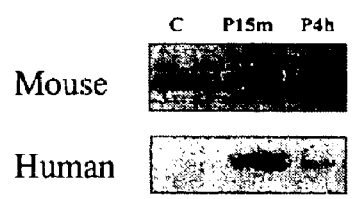
FIG. 1A and FIG. 1B: CREB phosphorylation following PACAP and cholera toxin treatment occurs in a reproducible manner in both mouse and human adult neural stem cells as shown by Western blotting. The upper panel shows up-regulation of CREB phosphorylation in mouse and human adult neural stem cells after PACAP pituitary adengate cyclase activating peptide treatment. The lower panel shows up-regulation of CREB phosphorylation in both mouse and human adult neural stem cells after cholera toxin treatment.
Figure 1:
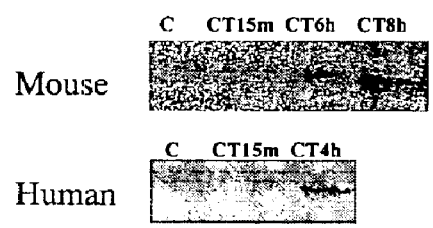

Traditional treatments of neural diseases and injuries have focused on the prevention of neuronal death (i.e., apoptosis or necrosis). In contrast, this invention is directed to novel therapeutic treatments for neurological diseases and injuries based on inducing neurogenesis, in particular, neural stem cell, or progenitor cell proliferation. In accordance with the invention, key neurogenesis modulating agents have been identified to induce proliferation and/or differentiation in neural cells. Such neurogenesis modulating agents are useful for effecting neurogenesis for the treatment of neurological diseases and injuries. As shown herein, increased levels of cAMP and/or $Ca^{2+}$ elicit the proliferation of adult neural stem cells. In some cases, this induction follows the activation of G-protein coupled receptors (GPCRs). The data disclosed herein indicate that increasing intracellular cAMP and/or $Ca^{2+}$ levels through various compounds (e.g., GPCR ligands) can be used to increase proliferation of adult neural stem cells. Furthermore, the data indicates that the progeny of the cells induced to proliferate by all the compounds analyzed, also retain their full neurogenic potential. Expression data for the GPCRs that bind to these ligands corroborate the importance of these two second messengers in promoting neurogenesis.

Proliferation data clearly shows that tissue culture cells and mice respond positively to the administration of neurogenesis modulating agents. The effects neurogenesis modulating agent administration includes neurogenesis in vivo and in vitro. See, e.g., the data presented in the Examples section.

"Neurogenesis" is defined herein as proliferation, differentiation, migration, or survival of a neural cell in vivo or in vitro. In a preferred embodiment, the neural cell is an adult, fetal, or embryonic neural stem cell or progenitor cell. Neurogenesis also refers to a net increase in cell number or a net increase in cell survival. As used herein, "NSC" would include, at least, all brain stem cells, all brain progenitor cells, and all brain precursor cells.

In this disclosure, the terms disease or disorder shall have the same meaning.

In this disclosure, the term analog shall also mean variants, fragments, and mimetics.

All the methods of the invention may be used on mammals and mammalian cells. In a preferred embodiment, all the methods of the invention may be used on humans or human cells.

Neural tissue includes, at least, all the tissues of the brain and central nervous system.

A neurogenesis modulating agent is defines as an agent or reagent that can promote neurogenesis. A number of novel neurogenesis modulating agent are disclosed in this invention including exendin and calcitonin.

Exendin-4 is a naturally occurring endocrine hormone that was originally isolated from the salivary of the lizard Heloderma suspectum (Eng J et al, J Biol Chem 1992; 267:7402–5). Exendin-4 exhibits several glucoregulatory effects including; glucose dependent enhancement of insulin secretion; glucose dependent suppression of high glucagon secretion; slowing of gastric emptying, reduction in food intake; lowering of blood pressure (revived in Nielsen LL et al, Regulatory Peptides 2004 117;77–88). In mammals Exendin-4 is resistant to degradation by dipeptidyl peptidase-IV (DPP-VI), whereas GLP-1 is degraded with a halftime less than 2 min (Kieffer T J et al, Endocrinology 1995; 136:3585–96). Exendin-4 is currently under clinical investigation (phase II and III) for treatment of Diabetes type II by Amylin pharmaceutical in collaboration with Lilly under the name exenatide:AC2993, AC002993, AC2993A, Exendin-4, or LY2148568 CAS# 141758-74-9 (Drugs RD 2004;5(1):35–40).

Studies have shown that intravenous injections of exendin-4 pass the mouse blood-brain barrier (BBB) and reach the brain intact (Kastin A J, Akerstrom V, Int J Obes Relat Metab Disord. 2003 March; 27(3):313–8). Interestingly, the homozygous mice GLP-1R knockout the animals shows contextual fear learning deficit. Additionally, Rats over expressing Glp1r shows improved learning and memory. Glp1r-deficient mice also have enhanced seizure severity and neuronal injury after kainate administration, which was reduced after Glp1r hippocampal gene transfer. The finding suggests a role for GLP1R and its ligands in learning and neuro-protection.

Calcitonin is secreted from the thyroid C cells and inhibits both basal and stimulated resorption of bone and reduces osteoclast numbers. Calcitonin is a 32-amino-acid-long peptide belonging to the class II secretin like superfamily of GPCRs.

For the purposes of this application, calcitonin and thyrocalcitonin include other molecules that are their analogs, derivatives, and hybrid molecules including calcitonin. These include, at least, molecules described in U.S. Pat. Nos. 6,713,452, 6,673,769, 6,617,423, 6,268,339, 6,265,534, 6,083,480, 6,028,168, 5,831,000, 4,658,014, 4,652,627, 4,644,054, 4,597,900, 4,497,731, 4,495,097, 4,451,395. These molecules include calcitonin drug or thyrocalcitonin drug which mean a drug possessing all or some of the biological activity of calcitonin or thyrocalcitonin respectively. These molecules also include calcitonin fragments or thyrocalcitonin fragments.

As used herein, the term "calcitonin" includes, at least, chicken calcitonin, eel calcitonin, human calcitonin, porcine calcitonin, rat calcitonin or salmon calcitonin provided by natural, synthetic, or genetically engineered sources.

As used herein, the term "calcitonin analog" or "thyrocalcitonin analog" means calcitonin or thyrocalcitonin wherein one or more of the amino acids have been replaced while retaining some or all of the activity of the calcitonin or thyrocalcitonin. The analog is described by noting the replacement amino acids with the position of the replacement as a superscript followed by a description of the calcitonin. For example, "$Pro_2$ calcitonin, human" means that the glycine typically found at the 2 position of a human calcitonin molecule has been replaced with proline.

Calcitonin or thyrocalcitonin analogs may be obtained by various means, as will be understood by those skilled in the art. For example, certain amino acids may be substituted for other amino acids in the calcitonin structure without appreciable loss of interactive binding capacity with structures such as, for example, antigen-binding regions of antibodies or binding sites on substrate molecules. As the interactive capacity and nature of calcitonin defines its biological functional activity, certain amino acid sequence substitutions can be made in the amino acid sequence and nevertheless remain a polypeptide with like properties.

As outlined above, amino acid substitutions are generally therefore based on the relative similarity of the amino acid side-chain substituents, for example, their hydrophobicity, hydrophilicity, charge, size, and the like. Exemplary substitutions (i.e., amino acids that may be interchanged without significantly altering the biological activity of the polypeptide) that take the foregoing characteristics into consideration are well known to those of skill in the art and include, for example: arginine and lysine; glutamate and aspartate; serine and threonine; glutamine and asparagine; and valine, leucine and isoleucine.

As used herein, the term "calcitonin fragment" means a segment of the amino acid sequence found in the calcitonin that retains some or all of the activity of the calcitonin. Similarly, the term "thyrocalcitonin fragment" means a segment of the amino acid sequence found in the thyrocalcitonin that retains some or all of the activity of the thyrocalcitonin.

The capability of a cell to divide without limit and produce daughter cells that terminally differentiate into neurons and glia are stem cell characteristics. Thus, the term "stem cell" (e.g., neural stem cell), as used herein, refers to an undifferentiated cell that can be induced to proliferate using the methods of the present invention. The stem cell is capable of self-maintenance, meaning that with each cell division, one daughter cell will also be a stem cell. The non-stem cell progeny of a stem cell are termed progenitor cells. The progenitor cells generated from a single multipotent stem cell are capable of differentiating into neurons, astrocytes (type I and type II) and oligodendrocytes. Hence, the stem cell is multipotent because its progeny have multiple differentiation pathways.

The term "progenitor cell" (e.g., neural progenitor cell), as used herein, refers to an undifferentiated cell derived from a stem cell, and is not itself a stem cell. Some progenitor cells can produce progeny that are capable of differentiating into more than one cell type. For example, an O-2A cell is a glial progenitor cell that gives rise to oligodendrocytes and type II astrocytes, and thus could be termed a bipotential progenitor cell. A distinguishing feature of a progenitor cell is that, unlike a stem cell, it has limited proliferative ability and thus does not exhibit self-maintenance. It is committed to a particular path of differentiation and will, under appropriate conditions, eventually differentiate into glia or neurons. The term "precursor cells", as used herein, refers to the progeny of stem cells, and thus includes both progenitor cells and daughter stem cells.

Neurogenesis Modulating Agents

One embodiment of the invention is directed to novel neurogenesis modulating agents that modulate intracellular levels of cAMP and/or $Ca^{2+}$. As used herein, neurogenesis modulating agent also include any substance that is chemically and biologically capable of increasing cAMP (e.g., by increasing synthesis or decreasing breakdown) and/or $Ca^{2+}$ (e.g., by increasing influx or decreasing efflux). These neurogenesis modulating agents include peptides, proteins, fusion proteins, chemical compounds, small molecules, and the like. Preferred for use with the invention are neurogenesis modulating agents comprising cAMP analogs, PDE inhibitors (e.g., cAMP-specific PDEs), adenylate cyclase activators, and activators of ADP-ribosylation of stimulatory G proteins.

Agents that have been shown in the experiments detailed herein to increase intracellular levels of cAMP include:

| Name | Peptide sequence | Identifier |
|---|---|---|
| Thyrocalcitonin salmon | Cys-Ser-Asn-Leu-Ser-Thr-Cys-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH2 | SEQ ID NO:1 |
| Calcitonin (Human) | Cys-Gly-Asn-Leu-Ser-Thr-Cys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro | SEQ ID NO:2 |
| Exendin-3 | His-Ser-Asp-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2 | SEQ ID NO:3 |
| Exendin-4 | His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2 | SEQ ID NO:4 |

Exemplary agents for increasing intracellular $Ca^{2+}$ levels include, but are not limited to the agents summarized in the table below:

| Name | Peptide sequence | Identifier |
|---|---|---|
| Amylin Receptor Antagonist/ Calcitonin (8–32) (Salmon). | Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro | SEQ ID NO:5 |
| CGRP (8–37) (Human) (Selective antagonist for CGRP receptor and agonist for Calcitonin receptor). | Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2 | SEQ ID NO:6 |
| amylin amide | Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr | SEQ ID NO:7 |

Calcitonin analogs also include, at least, the following: (1) Katacalcin; (2) Calcitonin-Gene-Related-Peptide (CGRP); (3) Calcitonin-Receptor-Stimulating-Peptides (CRSP)1, 2 or 3; (4) Orphan peptide PHM-27 (hCT receptor agonist); (5) Intermedin; (6) [Asp(17), Lys(21)] and [Asp(17), Orn(21)] side-chain bridged salmon calcitonin (sCT) and hCT analogues; (7) AC512 (Glaxo Wellcome and Amylin Pharmaceuticals); (8) Benzophenone-containing CT analogs (Pharmacol Exp Ther. 1997 November; 283(2):876–84); (9) Analogs of salmon calcitonin (sCT) [Arg11,18,Lys14]sCT; (10) Analogs of eel calcitonin (eCT) (Eur J Biochem. 1991 Nov. 1; 201(3):607–14). Each analog is described in more detail below.

Katacalcin (KC) belongs to a small family of polypeptides encoded by the calc-1 gene and also include calcitonin (CT) and procalcitonin. Katacalcin includes the amino acid sequence Asp-Met-Ser-Ser-Asp-Leu-Glu-Arg-Asp-His-Arg-Pro-His-Val-Ser-Met-Pro-Gln-Asn-Ala-Asn (SEQ ID NO:8) and analogs thereof. See, e.g., J Bone Miner Res. 2002 October; 17(10):1872–82.

Human calcitonin gene related peptide includes the amino acid sequence: Ala-Cys-Asp-Thr-Ala-Thr-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2 (SEQ ID NO:9) and analogs thereof.

Calcitonin receptor stimulating peptide 1 (CRSP-1) includes the amino acid sequence SCNTATCMTHR-LVGLLSRSGSMVRSNLLPTKMGFKVFG (SEQ ID NO:10) and analogs thereof. Calcitonin receptor stimulating peptide 2 (CRSP-2) includes the amino acid sequence SCN-TASCVTHKMTGWLSRSGSVAKNNFMPTNVDSKIL (SEQ ID NO:11) and analogs thereof. Calcitonin receptor stimulating peptide 3 (CRSP-3) includes the amino acid sequence SCNTAICVTHKMAGWLSRSGSVVKNN-FMPINMGSKVL (SEQ ID NO:12) and analogs thereof. See, e.g., Biochem Biophys Res Commun. 2003 Aug. 29; 308(3):445–51.

Histidine-methionine amide peptide hormone (PHM-27) includes the amino acid sequence His-Ala-Asp-Gly-Val-Phe-Thr-Ser-Asp-Phe-Ser-Lys-Leu-Leu-Gly-Gln-Leu-Ser-Ala-Lys-Lys-Tyr-Leu-Glu-Ser-Leu-Met-NH2 (SEQ ID NO:13) and analogs thereof. See, e.g., Biochem Pharmacol. 2004 Apr. 1; 67(7):1279–84.

Intermedin includes the amino acid sequence Thr-Gln-Ala-Gln-Leu-Leu-Arg-Val-Gly-Cys-Val-Leu-Gly-Thr-Cys-Gln-Val-Gln-Asn-Leu-Ser-His-Arg-Leu-Trp-Gln-Leu-Met-Gly-Pro-Ala-Gly-Arg-Gln-Asp-Ser-Ala-Pro-Val-Asp-Pro-Ser-Ser-Pro-His-Ser-Tyr-NH2 (SEQ ID NO:14) and analogs thereof. See, e.g., J Biol Chem. 2004 Feb. 20; 279(8): 7264–74.

Side-chain lactam-bridged analogs of human calcitonin (hCT) have been described (Kapurniotu, A.; et al. Eur. J. Biochem. 1999, 265, 606–618). Other side chain analogs of calcitonin, including a series of (Asp(17), Lys(21)) and (Asp(17), Orn(21)) side-chain bridged salmon calcitonin (sCT) and hCT have been synthesized. [Asp17, Lys21]-side-chain bridged salmon calcitonin includes the sequence Cys-Ser-Asn-Leu-Ser-Thr-Cys-Val-Leu-Gly-Lys-Leu-Ser-Gln-Asp-Leu-Asp-Lys-Leu-Gln-Lys-Phe-Pro-Arg-Thr-Asn-Thr-Gly-Ala-Gly-Val-Pro (SEQ ID NO:15), wherein Asp17 and Lys21 are linked by a lactam-bridge, and analogs thereof. [Asp17, Orn21]-side-chain bridged salmon calcitonin includes the sequence Cys-Ser-Asn-Leu-Ser-Thr-Cys-Val-Leu-Gly-Lys-Leu-Ser-Gln-Asp-Leu-Asp-Lys-Leu-Gln-Orn-Phe-Pro-Arg-Thr-Asn-Thr-Gly-Ala-Gly-Val-Pro (SEQ ID NO:16), wherein Asp17 and Orn21 are linked by a lactam-bridge, and analogs thereof. See, e.g., J Med Chem. 2002 Feb. 28; 45(5): 1108–21. For salmon calcitonin sequence and analogs, see, e.g., Hilton et al., 2000, J. Endocrinol. 166:213–226. For side-chain bridged analogs, see, e.g., Taylor et al., 2002, J. Med. Chem. 45:1108–1121.

[Lys11-Bolton Hunter, Arg18, Asn30, Tyr32]-salmon calcitonin (9–32) includes the sequence Leu-Gly-Lys-Leu-Ser-Gln-Asp-Leu-His-Arg-Leu-Gln-Thr-Phe-Pro-Arg-Thr-Asn-Thr-Gly-Ala-Asn-Val-Tyr (SEQ ID NO:17; also called AC512, Glaxo Wellcome and Amylin Pharmaceuticals), and analogs thereof.

Analogs of salmon calcitonin (sCT) have been synthesized (e.g., [Arg11, 18, Lys14]-salmon calcitonin) to provide a free amino group for derivatization. [Arg11, 18, Lys14]-salmon calcitonin includes the sequence Cys-Ser-Asn-Leu-Ser-Thr-Cys-Val-Leu-Gly-Arg-Leu-Ser-Lys-Asp-Leu-His-Arg-Leu-Gln-Thr-Phe-Pro-Arg-Thr-Asn-Thr-Gly-Ala-Gly-Val-Pro (SEQ ID NO:18). The potency of [Arg11, 18, Lys14]-sCT was found to be equivalent to that of sCT in activating adenylate cyclase in UMR 106-06 cells. The analog was derivatized with biotin, fluorescein, or 4-azidobenzoate without loss of activity. The derivatized analog was not degraded by lysine-specific endoprotease, whereas the underivatized [Arg11, 18, Lys14]-sCT was cleaved at Lys-14. The derivatized analogs were purified by HPLC and subsequently shown to possess full biological activity. The photoactive analog was used to photolabel 88,000 and 71,000 molecular weight components of the calcitonin receptor in rat osteoclasts, but only an 88,000 molecular weight component was photolabeled in the UMR 106-06 cells. See, e.g., Endocrinology. 1988 September; 123(3):1483–8; J Endocrinol. 2000 July; 166(1):213–26; Glaxo Wellcome; and Amylin Pharmaceuticals.

Benzophenone-containing calcitonin includes the calcitonin sequence Cys-Ser-Asn-Leu-Ser-Thr-Cys-Val-Leu-Gly-Lys-Leu-Ser-Gln-Asp-Leu-His-Lys-Leu-Gln-Thr-Phe-Pro-Arg-Thr-Asn-Thr-Gly-Ala-Gly-Val-Pro (SEQ ID NO:19), wherein all lysine residues are replaced with arginine, hydrophobic residues are replaced with a lysine(epsilon-p-benzoylbenzoyl) residues, Val8, Leu16 and Leu19 are replaced by lysine(epsilon-p-benzoylbenzoyl), and the N-terminus is acetylated by a p-Bz2 moiety. Benzophenone-containing calcitonin analogs are described in J Pharmacol Exp Ther. 1997 November; 283(2):876–84J Pharmacol Exp Ther. 1997 November; 283(2):876–84.

Eel calcitonin analog includes the sequence Asu-Ser-Asn-Leu-Ser-Thr-Asu-Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr-Pro-NH2 (SEQ ID NO:20). See, e.g., Eur J Biochem. 1991 Nov. 1; 201(3):607–14. Asu represents aminosuberic acid.

Exenatide is polypeptide with the amino acid sequence of HGEGTFTSDLSKQM EEEAVRLFIEWLKNGGPSSGAP-PPS (SEQ ID NO:21). Exenatide (also called AC002993, AC2993A, AC 2993, LY2148568, or Synthetic exendin-4, is available from Amylin Pharmaceuticals (San Diego, Calif., USA) and Eli Lilly and Co. (Indianapolis, Ind., USA ). Analogs of Exendin include, at least, the ones listed herein.

GLP-1 (Glucagon-like peptide-1) has an amino acid sequence of His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO:22). Other GLP-1 receptor ligand peptides include, HGEGTFTSDLSKMEE (SEQ ID NO:23), HGEGTFTSDLSKMEEE (SEQ ID NO:24), HSEGTFTS-DLSKMEE (SEQ ID NO:25), HAEGTFTSDLSKMEE (SEQ ID NO:26), HGEGTFTSD (SEQ ID NO:27), HAE-GTFTSDVSSYLEGQAAKEFIAWLVKGRG (SEQ ID NO:28) and HDEFERHAEGTFTSDVSSYLEGQAAKE-FIAWLVKGRG (SEQ ID NO:29). See, e.g., Diabetes 1998 47(2):159–69; Endocrinology. 2001 February; 142(2):521 –7; Curr Pharm Des. 2001 September; 7(14):1399–412.

GLP-1 analogs can exhibit one or more modifications of the N-terminal sequence of GLP-1, which includes the sequence HAEGTFTSDVS (SEQ ID NO:30). This encompasses [D-His1]-GLP-1, [Ac-His1]-GLP-1, desamino-GLP-1, [D-Ala2]-GLP-1, [Gly2]-GLP-1, [Ser2]-GLP-1, [D-Ala2, D-Asp8]-GLP-1, [D-Ala2, D-Ser8]-GLP-1, and [D-Ala2, D-Asp9]-GLP-1. See, e.g., Siegel et al., 1999, Regul. Pept. 79:93–102; Drucker et al., Gastroenterology. 2002 February; 122(2):531–44. For these analogs, D represents a D-amino acid, Ac represents an acetylated amino acid, and the first residue is designated as His1. Other N-terminal modifications of GLP-1(7–37) HAEGTFTSDVSSYLEGQAAKEFI-AWLVKGRG (SEQ ID NO:31) include [Thr8]-GLP-1 (7–37), [Gly8]-GLP-1 (7–37), [Ser8]-GLP-1 (7–36), and [Aib8]-GLP-1 (7–36). See, e.g., Deacon et al., 1998, Diabetologia 41:271–278. For these analogs, Aib represents 1-aminoisobutyric acid and the first residue is designated as His7. Other N-terminal modifications of GLP-1 include alpha-me-GLP-1 peptide with the structure:

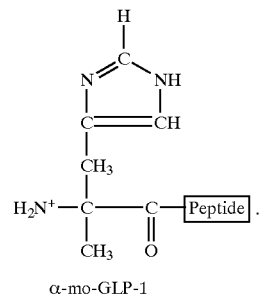

α-mo-GLP-1

Additional N-terminal modifications of GLP-1 include:

n-me-GLP-1   lmi-GLP-1 desamino-GLP-1

See, e.g., Gallwitz et al Regul Pept. 2000 Jan. 29; 86(1–3): 103–11.

CJC-1131 includes the amino acid sequence HAEGT-FTSDVSSYLEGQAAKEF IAWLVKGRK (SEQ ID NO:32), which has a single amino acid substitution of L-Ala8 to D-Ala8 and a Lys37 addition to the COOH-terminus with selective attachment of a [2-[2-[2-maleimidopropionamido(ethoxy)ethoxy]acetamide to the epsilon amino group of Lys37. For this analog, the first residue is designated as His7. CJC-1131 has been previously described (Kim et al., 2003, Diabetes 52:751–759) and is available from ConjuChem (Montreal, Quebec, Canada).

Liraglutide (also called NN-2211 and [Arg34, Lys26]-(N-epsilon-(gamma-Glu(N-alpha-hexadecanoyl))-GLP-1 (7–37)) includes the sequence HAEGTFTSDVS-SYLEGQAAKEFIAWKVRGRG (SEQ ID NO:33) and is available from Novo Nordisk (Denmark) or Scios (Fremont, Calif., USA). See, e.g., Elbrond et al., 2002, Diabetes Care. August; 25(8):1398404; Agerso et al., 2002, Diabetologia. February; 45(2):195–202.

Pramlintide (amylin analog) includes the sequence KCN-TATCATQRLANFLVH SSNNFGPILPPYNVGSNTY (SEQ ID NO:34) and is available from Amylin Pharmaceuticals (San Diego, Calif., USA) and Johnson and Johnson (New Brunswick, N.J. USA.)). Pramlintide is also called 25,28,29-pro-h-amylin and Symilin. See, e.g., Thompson et al., 1998, Diabetes Care, 21:987–993; Maggs et al., 2003, Metabolism. December; 52(12):163842; Whitehouse et al., 2002, Diabetes Care 25(4):724–30; Fineman et al., 2002, Metabolism 51(5):63641. Amylin is described in U.S. Pat. No. 5,367,052 as including the sequence KCNTATCATQR-LANFLVHSSNN FGAILSSTNVGSNTY (SEQ ID NO:35).

AVE-0010 (also called ZP-10) is available from Aventis (France).

[Ser(2)]-exendin (1–9) includes the sequence HSEGT-FTSD (SEQ ID NO:36) and has been described in Nature 1173–1179 (2003).

Still other neurogenesis modulating agents include PACAP receptors ligand peptides HSTGTFTSMDTSQLP (SEQ ID NO:37), HSTGTFTSMDT (SEQ ID NO:38), HST-GTFTSMD (SEQ ID NO:39), QSTGTFTSMD (SEQ ID NO:40), QTTGTFTSMD (SEQ ID NO:41) and HTTGT-FTSMD (SEQ ID NO:42).

The neurogenesis modulating agents (also referred to as the agents) of this disclosure are as listed in this section. It is understood that these neurogenesis modulating agent (agents) may be used, individually or in any combinations, wherever neurogenesis modulating agent or agents is specified in this specification. In one aspect of the invention "neurogenesis modulating agent" means any agents listed in this section. In another aspect of the invention, the neurogenesis modulating agent increases or maintains the amount of doublecortin positive cells or the percentage of doublecortin positive cells in a cell population or neural tissue.

Production of Neurogenesis Modulating Agents

Neurogenesis modulating agents may be produced using known techniques of chemical synthesis including the use of peptide synthesizers.

Neurogenesis modulating agents that are peptides and proteins may be synthesized chemically using commercially available peptide synthesizers. Chemical synthesis of peptides and proteins can be used for the incorporation of modified or unnatural amino acids, including D-amino acids and other small organic molecules. Replacement of one or more L-amino acids in a peptide or protein with the corresponding D-amino acid isoforms can be used to increase resistance to enzymatic hydrolysis, and to enhance one or more properties of biological activity, i.e., receptor binding, functional potency or duration of action.

Introduction of covalent cross-links into a peptide or protein sequence can conformationally and topographically constrain the peptide backbone for increased potency, selectivity, and stability. Other methods used successfully to introduce conformational constraints into amino acid sequences to improve their potency, receptor selectivity, and biological half-life include the use of (i) $C_\alpha$-methylamino acids (see, e.g., Rose, et al., Adv. Protein Chem. 37: 1–109 (1985); Prasad and Balaram, CRC Crit. Rev. Biochem., 16: 307–348 (1984)); (ii) $N_\alpha$-methylamino acids (see, e.g., Aubry, et al., Int. J. Pept. Protein Res., 18: 195–202 (1981); Manavalan and Momany, Biopolymers, 19: 1943–1973 (1980)); and (iii) $\alpha,\beta$-unsaturated amino acids (see, e.g., Bach and Gierasch, Biopolymers, 25: 5175-S192 (1986); Singh, et al., Biopolymers, 26: 819–829 (1987)). Additionally, replacement of the C-terminal acid with an amide can be used to enhance the solubility and clearance of a peptide or protein.

Alternatively, a neurogenesis modulating agent may be obtained by methods well known in the art for recombinant peptide or protein expression and purification. A DNA molecule encoding the neurogenesis modulating agent can be generated. The DNA sequence is known or can be deduced from the amino acid sequence based on known codon usage. See, e.g., Old and Primrose, Principles of Gene Manipulation 3$^{rd}$ ed., Blackwell Scientific Publications, 1985; Wada et al., Nucleic Acids Res. 20: 2111–2118(1992). Preferably, the DNA molecule includes additional sequences, e.g., recognition sites for restriction enzymes which facilitate its cloning into a suitable cloning vector, such as a plasmid. Nucleic acids may be DNA, RNA, or a combination thereof.

The biologically expressed neurogenesis modulating agent may be purified using known purification techniques. An "isolated" or "purified" recombinant peptide or protein, or biologically active portion thereof, means that said peptide or protein is substantially free of cellular material or other contaminating proteins from the cell or tissue source from which it is derived. The language "substantially free of cellular material" includes preparations in which the peptide or protein is separated from cellular components of the cells from which it is isolated or recombinantly produced. In one embodiment, the language "substantially free of cellular material" includes preparations of peptide or protein having less than about 30% (by dry weight) of product other than the desired peptide or protein (also referred to herein as a "contaminating protein"), more preferably less than about 20% of contaminating protein, still more preferably less than about 10% of contaminating protein, and most preferably less than about 5% contaminating protein. When the peptide or protein, or biologically active portion thereof, is recombinantly produced, it is also preferably substantially free of culture medium, i.e., culture medium represents less than about 20%, more preferably less than about 10%, and most preferably less than about 5% of the volume of the peptide or protein preparation.

The invention also pertains to variants and derivatives of a neurogenesis modulating agent that function as either agonists (mimetics) or partial agonists. Variants of a neurogenesis modulating agent can be generated by mutagenesis, e.g., discrete point mutations. An agonist of a neurogenesis modulating agent can retain substantially the same, or a subset of, the biological activities of the naturally occurring form of the neurogenesis modulating agent. Thus, specific biological effects can be elicited by treatment with a variant with a limited function. In one embodiment, treatment of a subject with a variant having a subset of the biological activities of the naturally occurring form of the neurogenesis modulating agent has fewer side effects in a subject relative to treatment with the non-variant neurogenesis modulating agent.

Preferably, the analog, variant, or derivative neurogenesis modulating agent is functionally active. As utilized herein, the term "functionally active" refers to species displaying one or more known functional attributes of neurogenesis. "Variant" refers to a neurogenesis modulating agent differing from naturally occurring neurogenesis modulating agent, but retaining essential properties thereof.

Variants of the neurogenesis modulating agent that function as agonists (mimetics) can be identified by screening combinatorial libraries of mutants of the neurogenesis modulating agent for peptide or protein agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential sequences is expressible as individual peptides, or alternatively, as a set of larger fusion proteins (e.g., for phage display) containing the set of sequences therein. There are a variety of methods that can be used to produce libraries of potential variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential sequences.

Derivatives and analogs of a neurogenesis modulating agent of the invention or individual moieties can be produced by various methods known within the art. For example, the amino acid sequences may be modified by any number of methods known within the art. See e.g., Sambrook, et al., 1990. Molecular Cloning: A Laboratory Manual, 2nd ed., (Cold Spring Harbor Laboratory Press; Cold Spring Harbor, N.Y.). Modifications include: glycosylation, acetylation, phosphorylation, amidation, derivatization by known protecting/blocking groups, linkage to an antibody molecule or other cellular reagent, and the like. Any of the numerous chemical modification methodologies known within the art may be utilized including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Derivatives and analogs may be full length or other than full length, if said derivative or analog contains a modified nucleic acid or amino acid, as described infra. Derivatives or analogs of the neurogenesis modulating agent include, but are not limited to, molecules comprising regions that are substantially homologous in various embodiments, of at least 30%, 40%, 50%, 60%, 70%, 80%, 90% or preferably 95% amino acid identity when: (i) compared to an amino acid sequence of identical size; (ii) compared to an aligned sequence in that the alignment is done by a computer homology program known within the art (e.g., Wisconsin GCG software) or (iii) the encoding nucleic acid is capable of hybridizing to a sequence encoding the aforementioned peptides under stringent (preferred), moderately stringent, or non-stringent conditions. See, e.g., Ausubel, et al., Current Protocols in Molecular Biology, John Wiley and Sons, New York, N.Y., 1993.

Derivatives of a neurogenesis modulating agent of the invention may be produced by alteration of their sequences by substitutions, additions, or deletions that result in functionally equivalent molecules. One or more amino acid residues within the neurogenesis modulating agent may be substituted by another amino acid of a similar polarity and net charge, thus resulting in a silent alteration. Conservative substitutes for an amino acid within the sequence may be selected from other members of the class to which the amino acid belongs. For example, nonpolar (hydrophobic) amino acids include alanine, leucine, isoleucine, valine, proline, phenylalanine, tryptophan, and methionine. Polar neutral amino acids include glycine, serine, threonine, cysteine, tyrosine, asparagine, and glutamine. Positively charged (basic) amino acids include arginine, lysine, and histidine. Negatively charged (acidic) amino acids include aspartic acid and glutamic acid.

Neurogenesis modulating agents also include functional mimetic. A functional mimetic means a substance that may not contain an active portion of a protein or peptide but, and probably is not a peptide at all, but which has the property of binding to a receptor for the peptide or protein.

Compositions Comprising Neurogenesis Modulating Agent(s) and their Administration Another embodiment of the invention is directed to pharmaceutical compositions comprising a neurogenesis modulating agent of the invention. The neurogenesis modulating agents of the invention can be formulated into pharmaceutical compositions that can be used as therapeutic agents for the treatment of neurological diseases (disorders). These compositions are discussed in this section. It is understood that any pharmaceutical compositions and chemicals discussed in this section can be a component of a pharmaceutical composition comprising one or more neurogenesis modulating agents.

Neurogenesis modulating agents, derivatives, and co-administered agents can be incorporated into pharmaceutical compositions suitable for administration. Such compositions typically comprise the agent and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the agents to affect solubility or clearance of the peptide. Peptidic molecules may also be synthesized with D-amino acids to increase resistance to enzymatic degradation. In some cases, the composition can be co-administered with one or more solubilizing agents, preservatives, and permeation enhancing agents.

Preferably, the pharmaceutical composition is used to treat diseases by stimulating neurogenesis (i.e., cell growth, proliferation, migration, survival and/or differentiation). For treatment, a method of the invention comprises administering to the subject an effective amount of a pharmaceutical composition including an agent of the invention (1) alone in a dosage range of 0.001 ng/kg/day to 500 ng/kg/day, preferably in a dosage range of 0.05 to 150 or up to 300 ng/kg/day, (2) in a combination permeability increasing factor, or (3) in combination with a locally or systemically co-administered agent. The level of administration may be at least 0.001 ng/kg/day, at least 0.01 ng/kg/day, 0.1 ng/kg/day, at least 1 ng/kg/day, at least 5 mg/kg/day, at least 10 mg/kg/day, or at least 50 mg/kg/day. In a preferred embodiment, the administration raises the intracellular levels of cAMP at least 20% above normal. The administration may lead to tissue concentrations of the agent of about 0.0001 nM to 50 nM.

A pharmaceutical composition of the invention is formulated to be compatible with its intended route of administration. Such compositions are known. The parenteral preparation can be enclosed in ampoules, disposable syringes or multiple dose vials made of glass or plastic.

Oral administration refers to the administration of the formulation via the mouth through ingestion, or via any other part of the gastrointestinal system including the esophagus or through suppository administration. Parenteral administration refers to the delivery of a composition, such as a composition comprising a neurogenesis modulating agent by a route other than through the gastrointestinal tract (e.g., oral delivery). In particular, parenteral administration may be via intravenous, subcutaneous, intramuscular or intramedullary (i.e., intrathecal) injection. Topical administration refers to the application of a pharmaceutical agent to the external surface of the skin or the mucous membranes (including the surface membranes of the nose, lungs and mouth (in which case it may also be a form of oral administration, such that the agent crosses the external surface of the skin or mucous membrane and enters the underlying tissues. Topical administration of a pharmaceutical agent can result in a limited distribution of the agent to the skin and surrounding tissues or, when the agent is removed from the treatment area by the bloodstream, can result in systemic distribution of the agent.

In a preferred form of topical administration, the neurogenesis promoting agent is delivered by transdermal delivery. Transdermal delivery refers to the diffusion of an agent across the barrier of the skin. Absorption through intact skin can be enhanced by placing the active agent in an oily vehicle before application to the skin (a process known as inunction) and the use of microneedles. Passive topical administration may consist of applying the active agent directly to the treatment site in combination with emollients or penetration enhancers. Another method of enhancing delivery through the skin is to increase the dosage of the pharmaceutical agent. The dosage for topical administration may be increased up to ten, a hundred or a thousand folds more than the usual dosages stated elsewhere in this disclosure.

In addition, the medicament and neurogenesis modulating agents of the invention may be delivered by nasal or pulmonary methods. The respiratory delivery of aerosolized medicaments is described in a number of references, beginning with Gansslen (1925) Klin. Wochenschr. 4:71 and including Laube et al. (1993) JAMA 269:2106–21–9; Elliott et al. (1987) Aust. Paediatr. J. 23:293–297; Wigley et al. (1971) Diabetes 20:552–556. Corthorpe et al. (1992) Pharm Res 9:764–768; Govinda (1959) Indian J. Physiol. Pharmacol. 3:161–167; Hastings et al. (1992) J. Appl. Physiol. 73:1310–1316; Liu et al. (1993) JAMA 269:2106–2109; Nagano et al. (1985) Jikeikai Med. J. 32:503–506; Sakr (1992) Int. J. Phar. 86:1–7; and Yoshida et al. (1987) Clin. Res. 35:160–166. Pulmonary delivery of dry powder medicaments is described in U.S. Pat. No. 5,254,330. A metered dose inhaler is described in Lee and Sciara (1976) J. Pharm. Sci. 65:567–572. The intrabronchial administration of recombinant insulin is briefly described in Schlutiter et al. (Abstract) (1984) Diabetes 33:75A and Kohler et al. (1987) Atemw. Lungenkrkh. 13:230–232. Intranasal and respiratory delivery of a variety of polypeptides are described in U.S. Pat. No. 5,011,678 and Nagai et al. (1984) J. Contr. Rel. 1:15–22.

Pharmaceutical compositions suitable for injectable use include sterile aqueous solutions (where water soluble) or dispersions and sterile powders for the extemporaneous preparation of sterile injectable solutions or dispersion. For intravenous administration, physiologically acceptable, suitable carriers include physiological saline, bacteriostatic water, Cremophor EL™ (BASF, Parsippany, N.J.) or phosphate buffered saline (PBS).

Physiologically acceptable carriers maybe any carrier known in the field as suitable for pharmaceutical (i.e., topical, oral, and parenteral) application. Suitable pharmaceutical carriers and formulations are described, for example, in Remington's Pharmaceutical Sciences (19th ed.) (Genarro, ed. (1995) Mack Publishing Co., Easton, Pa.).

Oral compositions generally include a physiologically acceptable, inert diluent or an edible carrier. They can be enclosed in gelatin capsules or compressed into tablets. For the purpose of oral therapeutic administration, the neurogenesis modulating agent of the invention can be incorporated with physiological excipients and used in the form of tablets, troches, or capsules.

A number of systems that alter the delivery of injectable drugs can be used to change the pharmacodynamic and pharmacokinetic properties of therapeutic agents (see, e.g., K. Reddy, 2000, Annals of Pharmacotherapy 34:915–923). Drug delivery can be modified through a change in formulation (e.g., continuous-release products, liposomes) or an addition to the drug molecule (e.g., pegylation). Potential advantages of these drug delivery mechanisms include an increased or prolonged duration of pharmacologic activity, a decrease in adverse effects, and increased patient compliance and quality of life. Injectable continuous-release systems deliver drugs in a controlled, predetermined fashion and are particularly appropriate when it is important to avoid large fluctuations in plasma drug concentrations. Encapsulating a drug within a liposome can produce a prolonged half-life and an increased distribution to tissues with increased capillary permeability (e.g., tumors). Pegylation provides a method for modification of therapeutic peptides or proteins to minimize possible limitations (e.g., stability, half-life, immunogenicity) associated with these neurogenesis modulating agents.

In accordance with the invention, one or more neurogenesis modulating agents can be formulated with lipids or lipid vehicles (e.g., micells, liposomes, microspheres, protocells, protobionts, liposomes, coacervates, and the like) to allow formation of multimers. Similarly, neurogenesis modulating agents can be multimerized using pegylation, cross-linking, disulfide bond formation, formation of covalent cross-links, glycosylphosphatidylinositol (GPI) anchor formation, or other established methods. The multimerized neurogenesis modulating agent can be formulated into a pharmaceutical composition, and used to increase or enhance their effects.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For administration by inhalation, the neurogenesis modulating agents of the invention can be delivered in the form of an aerosol spray from pressured container or dispenser that contains a suitable propellant, e.g., a gas such as carbon dioxide, or a nebulizer. For transdermal administration, the neurogenesis modulating agents of the invention can be formulated into ointments, salves, gels, or creams as generally known in the art.

The neurogenesis modulating agents can also be prepared in the form of suppositories (e.g., with conventional suppository bases such as cocoa butter and other glycerides) or retention enemas for rectal delivery.

In one embodiment, the neurogenesis modulating agent of the invention are prepared with carriers that will protect the neurogenesis modulating agent against rapid elimination from the body, such as a controlled release formulation, including implants and microencapsulated delivery systems. These can be prepared according to methods known to those skilled in the art, for example, as described in U.S. Pat. No. 4,522,811.

Compositions that include one or more neurogenesis modulating agents of the invention can be administered in any conventional form, including in any form known in the art in which it may either pass through or by-pass the blood-brain barrier. Methods for allowing factors to pass through the blood-brain barrier include minimizing the size of the factor, providing hydrophobic factors which may pass through more easily, conjugating the protein neurogenesis modulating agent or other agent to a carrier molecule that has a substantial permeability coefficient across the blood brain barrier (see, e.g., U.S. Pat. No. 5,670,477).

In some instances, the neurogenesis modulating agent can be administered by a surgical procedure implanting a catheter coupled to a pump device. The pump device can also be implanted or be extracorporally positioned. Administration of the neurogenesis modulating agent can be in intermittent pulses or as a continuous infusion. Devices for injection to discrete areas of the brain are known in the art (see, e.g., U.S. Pat. Nos. 6,042,579; 5,832,932; and 4,692,147).

Method for Reducing a Symptom of a Disorder by Administering Neurogenesis Modulating Agent(s)

One embodiment of the invention is directed to a method for reducing a symptom of a disorder in a patient by administering a neurogenesis modulating agent of the invention to the patient. In that method, one or more neurogenesis modulating agent is directly administered to the animal, which will induce additional proliferation and/or differentiation of a neural tissue of said animal. Such in vivo treatment methods allows disorders caused by cells lost, due to injury or disease, to be endogenously replaced. This will obviate the need for transplanting foreign cells into a patient A neurogenesis modulating agent of the invention can be administered systemically to a patient. In a preferred embodiment, the neurogenesis modulating agent is administered locally to any loci implicated in the CNS disorder pathology, i.e. any loci deficient in neural cells as a cause of the disease. For example, the neurogenesis modulating agent can be administered locally to the ventricle of the brain, substantia nigra, striatum, locus ceruleous, nucleus basalis Meynert, pedunculopontine nucleus, cerebral cortex, and spinal cord. Preferably, a central nervous system disorder includes neurodegenerative disorders, ischemic disorders, neurological traumas, and learning and memory disorders.

The method of the invention takes advantage of the fact that stem cells are located in the tissues lining ventricles of mature brains offers. Neurogenesis may be induced by administering a neurogenesis modulating agent of the invention directly to these sites and thus avoiding unnecessary systemic administration and possible side effects. It may be desireable to implant a device that administers the composition to the ventricle and thus, to the neural stem cells. For example, a cannula attached to an osmotic pump may be used to deliver the composition. Alternatively, the composition may be injected directly into the ventricles. The cells can migrate into regions that have been damaged as a result of injury or disease. Furthermore, the close proximity of the ventricles to many brain regions would allow for the diffusion of a secreted neurological agent by the cells (e.g., stem cells or their progeny).

The invention provides a method for inducing neurogenesis in vivo or in vitro, which can be used to treat various diseases and disorders of the CNS as described in detail herein. The term "treating" in its various grammatical forms in relation to the present invention refers to preventing, curing, reversing, attenuating, alleviating, ameliorating minimizing, suppressing, or halting the deleterious effects of a neurological disorder, disorder progression, disorder causative agent (e.g., bacteria or viruses), injury, trauma, or other abnormal condition. Symptoms of neurological disorders include, but are not limited to, tension, abnormal movements, abnormal behavior, tics, hyperactivity, combativeness, hostility, negativism, memory defects, sensory defects, cognitive defects, hallucinations, acute delusions, poor self-care, and sometimes withdrawal and seclusion.

Abnormal movement symptoms include a wide variety of symptoms that can range from unconscious movements that interfere very little with quality of life, to quite severe and disabling movements. Examples of symptoms which are seen associated with neurological disorders include involuntary tongue protrusions, snake-like tongue movements, repetitive toe and finger movements, tremors of extremities or whole body sections, tics, muscular rigidity, slowness of movement, facial spasms, acute contractions of various muscles, particularly of the neck and shoulder which may eventually lead to painful, prolonged muscle contraction, restlessness, distress and an inability to remain still. Abnormal behavioral symptoms, some of which are motor in nature, include irritability, poor impulse control, distractibility, aggressiveness, and stereotypical behaviors that are commonly seen with mental impairment such as rocking, jumping, running, spinning, flaying, etc.

Any of the methods of the invention may be used to alleviate a symptom of a neurological disease or disorder such as Parkinson's disease (shaking palsy), including primary Parkinson's disease, secondary parkinsonism, and postencephalitic parkinsonism; drug-induced movement disorders, including parkinsonism, acute dystonia, tardive dyskinesia, and neuroleptic malignant syndrome; Huntington's disease (Huntington's chorea; chronic progressive chorea; hereditary chorea); delirium (acute confusional state); dementia; Alzheimer's disease; non-Alzheimer's dementias, including Lewy body dementia, vascular dementia, Binswanger's dementia (subcortical arteriosclerotic encephalopathy), dementia pugilistica, normal-pressure hydrocephalus, general paresis, frontotemporal dementia, multi-infarct dementia, and AIDS dementia; age-associated memory impairment (AAMI); amnesias, such as retrograde, anterograde, global, modality specific, transient, stable, and progressive amnesias, and posttraumatic amnesias, and Korsakoffs disease.

Other diseases and disorders include idiopathic orthostatic hypotension, Shy-Drager syndrome, progressive supranuclear palsy (Steele-Richardson-Olszewski syndrome); structural lesions of the cerebellum, such as those associated with infarcts, hemorrhages, or tumors; spinocerebellar degenerations such as those associated with Friedreich's ataxia, abetalipoproteinemia (e.g., Bassen-Kornzweig syndrome, vitamin E deficiency), Refsum's disease (phytanic acid storage disease), cerebellar ataxias, multiple systems atrophy (olivopontocerebellar atrophy), ataxia-telangiectasia, and mitochondrial multisystem disorders; acute disseminated encephalomyelitis (postinfectious encephalomyelitis); adrenoleukodystrophy and adrenomyeloneuropathy; Leber's hereditary optic atrophy; HTLV-associated myelopathy; and multiple sclerosis; motor neuron disorders such as amyotrophic lateral sclerosis, progressive bulbar palsy, progressive muscular atrophy, primary lateral sclerosis and progressive pseudobulbar palsy, and spinal muscular atrophies such as type I spinal muscular atrophy (Werdnig-Hoffman disease), type II (intermediate) spinal muscular atrophy, type III spinal muscular atrophy (Wohlfart-Kugelberg-Welander disease), and type IV spinal muscular atrophy.

Further diseases and disorders include plexus disorders such as plexopathy and acute brachial neuritis (neuralgic amyotrophy); peripheral neuropathies such as mononeuropathies, multiple mononeuropathies, and polyneuropathies, including ulnar nerve palsy, carpal tunnel syndrome, peroneal nerve palsy, radial nerve palsy, Guillain-Barre syndrome (Landry's ascending paralysis; acute inflammatory demyelinating polyradiculoneuropathy), chronic relapsing polyneuropathy, hereditary motor and sensory neuropathy, e.g., types I and II (Charcot-Marie-Tooth disease, peroneal muscular atrophy), and type III (hypertrophic interstitial neuropathy, Dejerine-Sottas disease); disorders of neuromuscular transmission, such as myasthenia gravis; neuro-ophthalmologic disorders such as Horner's syndrome, internuclear ophthalmoplegia, gaze palsies, and Parinaud's syndrome; cranial nerve palsies, trigeminal neuralgia (Tic Douloureux); Bell's palsy; and glossopharyngeal neuralgia; radiation-induced injury of the nervous system; chemotherapy-induced neuropathy (e.g., encephalopathy); taxol neuropathy; vincristine neuropathy; diabetic neuropathy; autonomic neuropathies; polyneuropathie;, and mononeuropathies; and ischemic syndromes such as transient ischemic attacks, subclavian steal syndrome, drop attacks, ischemic stroke, hemorrhagic stroke, and brain infarction.

For treatment of Huntington's disease, Alzheimer's disease, Parkinson's disease, and other neurological disorders affecting primarily the forebrain, one or more of the disclosed neurogenesis modulating agents, with or without growth factors or other neurological agents would be delivered to the ventricles of the forebrain to affect in vivo modification or manipulation of the cells. The disclosed neurogenesis modulating agents could also be delivered via a systemic route (oral, injection) but still execute their effect at specific sites in the brain (e.g. the ventricles). For example, Parkinson's disease is the result of low levels of dopamine in the brain, particularly the striatum. It would be advantageous to induce a patient's own quiescent stem cells to begin to divide in vivo, thus locally raising the levels of dopamine. The methods and compositions of the present invention provide an alternative to the use of drugs and the controversial use of large quantities of embryonic tissue for treatment of Parkinson's disease. Dopamine cells can be generated in the striatum by the administration of a composition comprising growth factors to the lateral ventricle. A particularly preferred composition comprises one or more of the neurogenesis modulating agents disclosed herein. While preferred embodiments of specific delivery have been disclosed, it is understood that the neurogenesis modulating agents disclosed herein could also be effective via systemic delivery using any of the methods of administration discussed in this disclosure.

For the treatment of MS and other demyelinating or hypomyelinating disorders, and for the treatment of Amyotrophic Lateral Sclerosis or other motor neuron diseases, one or more of the disclosed neurogenesis modulating agents, with or without growth factors or other neurological agents would be delivered to the central canal. In addition to treating CNS tissue immediately surrounding a ventricle, a viral vector, DNA, growth factor, or other neurological agent can be easily administered to the lumbar cistern for circulation throughout the CNS. Infusion of EGF or similar growth factors can be used with the neurogenesis modulating agents of the invention to enhance the proliferation, migration, and differentiation of neural stem cells and progenitor cells in vivo (see, e.g., U.S. Pat. No. 5,851,832). In a preferred embodiment EGF and FGF are administered together or sequentially with the neurogenesis modulating agents disclosed herein.

The blood-brain barrier can be bypassed by in vivo transfection of cells with expression vectors containing genes that code for neurogenesis modulating agents, so that the cells themselves produce the neurogenesis modulating agents. Any useful genetic modification of the cells is within the scope of the present invention. For example, in addition to genetic modification of the cells to express neurogenesis modulating agents, the cells may be modified to express other types of neurological agents such as neurotransmitters. Preferably, the genetic modification is performed either by infection of the cells lining ventricular regions with recombinant retroviruses or transfection using methods known in the art including $CaPO_4$ transfection, DEAE-dextran transfection, polybrene transfection, by protoplast fusion, electroporation, lipofection, and the like see Maniatis et al., supra. Any method of genetic modification, now known or later developed can be used.

The methods of the invention can be used to treat any mammal, including humans, cows, horses, dogs, sheep, and cats. Preferably, the methods of the invention are used to treat humans. In one aspect, the invention provides a regenerative treatment for neurological disorders by stimulating cells (e.g., stem cells) to grow, proliferate, migrate, survive, and/or differentiate to replace neural cells that have been lost or destroyed. In vivo stimulation of such cells (e.g., stem cells) can be accomplished by locally administering (via any route) a neurogenesis modulating agent of the invention to the cells in an appropriate formulation. By increasing neurogenesis, damaged or missing cells can be replaced in order to enhance blood function.

Methods for preparing the neurogenesis modulating agent dosage forms are known, or will be apparent, to those skilled in this art. The determination of an effective amount of a neurogenesis modulating agent to be administered in within the skill of one of ordinary skill in the art and will be routine to those persons skilled in the art. The amount of neurogenesis modulating agent to be administered will depend upon the exact size and condition of the patient, but will be at least 0.1 ng/kg/day, at least 1 ng/kg/day, at least 5 ng/kg/day, at least 20 ng/kg/day, at least 100 ng/kg/day, at least 0.5 µg/kg/day, at least 2 µg/kg/day, at least 5 µg/kg/day, at least 50 µg/kg/day, at least 500 µg/kg/day, at least 1 mg/kg/day, at least 5 mg/kg/day, or at least 10 mg/kg/day in a volume of 0.001 to 10 ml. In another method of dosage, the modulator may be administered so that a target tissue achieves a modulator concentration of 0.0001 nM to 50 nM, 0.001 nM to 50 nM, 0.01 nM to 50 nM, 0.1 nM to 50 nM, 0.1 nM to 100 nM, or at least 1 nM, at least 50 nM, or at least 100 nM. Preferred dosages include subcutaneous administration of at least 10 mg twice a week or at least 25 mg twice a week;

subcutaneous administration of at least 0.04 mg/kg/week, at least 0.08 mg/kg/week, at least 0.24 mg/kg/week, at least 36 mg/kg/week, or at least 48 mg/kg/week; subcutaneous administration of at least 22 mcg twice a week or 44 mcg twice a week; or intravenous administration of at least 3–10 mg/kg once a month. Particularly preferred dosage ranges are 0.04 mg/kg to 4 mg/kg and 0.05 mg/kg to 5 mg/kg. These dosages may be increased 10×, 100×, or 1000× in transdermal or topical applications.

Pharmaceutical compositions suitable for use in the present invention include compositions wherein the active ingredients are contained in an effective amount to achieve its intended purpose. More specifically, a therapeutically effective amount means an amount effective to optimally stimulate or suppress cell (e.g., stem cell or progenitor cell) proliferation. It will be appreciated that the unit content of active ingredient or ingredients contained in an individual dose of each dosage form need not in itself constitute an effective amount since the necessary effective amount can be reached by administration of a plurality of dosage units (such as capsules or tablets or combinations thereof). In addition, it is understood that at some dosage levels, an effective amount may not show any measurable effect (the measurable effect could be lack of deterioration) until after a week, a month, three months, or six months of usage. Further, it is understood that an effective amount may lessen the rate of the natural deterioration that comes with age but may not reverse the deterioration that has already occurred. Determination of the effective amounts is well within the capability of those skilled in the art, especially in light of the detailed disclosure provided herein. The specific dose level for any particular user will depend upon a variety of factors including the activity of the specific neurogenesis modulating agent employed, the age, the physical activity level, general health, and the severity of the disorder.

A therapeutically effective dose also refers to that amount necessary to achieve the desired effect without unwanted or intolerable side effects. Toxicity and therapeutic efficacy of a neurogenesis modulating agent of the invention can be determined by standard pharmaceutical procedures in cell cultures or experimental animals. Using standard methods, the dosage that shows effectiveness in about 50% of the test population, the $ED_{50}$, may be determined. Effectiveness may be any sign of cell (e.g., stem cell) proliferation or suppression. Similarly, the dosage that produces an undesirable side effect to 50% of the population, the $SD_{50}$, can be determined. Undesirable side effects include death, wounds, rashes, abnormal redness, and the like. The dose ratio between side effect and therapeutic effects can be expressed as the therapeutic index and it can be expressed as a ratio between $SD_{50}/ED_{50}$. Neurogenesis modulating agents with high therapeutic indexes are preferred, i.e., neurogenesis modulating agents that are effective at low dosage and which do not have undesirable side effects until very high doses. A preferred therapeutic index is greater than about 3, more preferably, the therapeutic index is greater than 10, most preferably the therapeutic index is greater than 25, such as, for example, greater than 50. Furthermore, neurogenesis modulating agents that do not have side effects at any dosage levels are more preferred. Finally, neurogenesis modulating agents that are effective at low dosages and do not have side effects at any dosage levels are most preferred. The exact formulation, route of administration and dosage can be chosen depending on the desired effect and can be made by those of skill in the art.

Dosage intervals can be determined by experimental testing. One or more neurogenesis modulating agents of the invention should be administered using a regimen which maintains cell (e.g., stem cell) proliferation at about 10% above normal, about 20% above normal, above 50% above normal such as 100% above normal, preferably about 200% above normal, more preferably about 300% above normal and most preferably about 500% above normal. In a preferred embodiment, the pharmaceutical composition of the invention may comprise a neurogenesis modulating agent of the invention at a concentration of between about 0.001% to about 10%, preferably between about 0.01% and about 3%, such as, for example, about 1% by weight.

Another suitable administration method is to provide a neurogenesis modulating agent of the invention through an implant or a cell line capable of expressing a neurogenesis modulating agent (e.g., peptide neurogenesis modulating agent) so that the implant or cell line can provide the neurogenesis modulating agent to a cell of the CNS.

In a preferred embodiment of the invention, the neurogenesis modulating agent of the invention induces neurogenesis in a patient. In a more preferred embodiment, the neurogenesis modulating agent induces neurogenesis in at least the lateral ventricle wall region or the hippocampus region of the brain. In a more preferred embodiment, the neurogenesis modulating agent induces neurogenesis in the lateral ventricle wall but not in the hippocampus.

The methods of the invention may be used to detect endogenous agents in cells (e.g., neural stem cells, neural progenitor cells) can be identified using RT-PCR or in situ hybridization techniques. In particular, genes that are up regulated or down regulated in these cells in the presence of one or more neurogenesis modulating agent of the invention can be identified. The regulation of such genes may indicate that they are involved in the mediation of signal transduction pathways in the regulation of neurogenesis function. Furthermore, by knowing the levels of expression of the these genes, and by analyzing the genetic or amino-acid sequence variations in these genes or gene products, it may be possible to diagnose disease or determine the role of cells (e.g., stem and progenitor cells) in the disease. Such analysis will provide important information for using cell-based treatments for disease.

Method for Reducing a Symptom of a Disorder by Administering Cells Treated with Neurogenesis Modulating Agent(s)

Harvesting Cells and Inducing Neurogenesis:

Another embodiment of the invention is directed to a method for inducing cells (e.g., stem cells or progenitor cells) to undergo neurogenesis in vitro—to generate large numbers of neural cells capable of differentiating into neurons, astrocytes, and oligodendrocytes. The induction of proliferation and differentiation of cells (e.g., stem cells or progenitor cells) can be done either by culturing the cells in suspension or on a substrate onto which they can adhere. The induced cells may be used for therapeutic treatment. For example, therapy may involve, at least, (1) proliferation and differentiation of neural cells in vitro, then transplantation, (2) proliferation of neural cells in vitro, transplantation, then further proliferation and differentiation in vivo, (3) proliferation in vitro, transplantation and differentiation in vivo, and (4) proliferation and differentiation in vivo. Thus, the invention provides a means for generating large numbers of cells for transplantation into the neural tissue of a host in order to treat neurodegenerative disease and neurological trauma, for non-surgical methods of treating neurodegenerative disease and neurological trauma, and for drug-screening applications.

Stem cell progeny can be used for transplantation into a heterologous, autologous, or xenogeneic host. Multipotent stem cells can be obtained from embryonic, post-natal, juvenile, or adult neural tissue, or other tissues. Human heterologous stem cells may be derived from fetal tissue following elective abortion, or from a post-natal, juvenile, or adult organ donor. Autologous tissue can be obtained by biopsy, or from patients undergoing surgery (e.g., neurosurgery) in which tissue is removed, for example, during epilepsy surgery, temporal lobectomies, and hippocampalectomies. Stem cells have been isolated from a variety of adult CNS ventricular regions and proliferated in vitro using the methods detailed herein. In various embodiments of the invention, the tissue can be obtained from any animal, including insects, fish, reptiles, birds, amphibians, mammals and the like. The preferred source of tissue (e.g., neural tissue) is from mammals, preferably rodents and primates, and most preferably, mice and humans.

In the case of a heterologous donor animal, the animal may be euthanized, and the neural tissue and specific area of interest removed using a sterile procedure. Areas of particular interest include any area from which neural stem cells can be obtained that will serve to restore function to a degenerated area of the host's nervous system, particularly the host's CNS. Suitable areas include the cerebral cortex, cerebellum, midbrain, brainstem, spinal cord and ventricular tissue, and areas of the PNS including the carotid body and the adrenal medulla. Preferred areas include regions in the basal ganglia, preferably the striatum which consists of the caudate and putamen, or various cell groups such as the globus pallidus, the subthalamic nucleus, the nucleus basalis which is found to be degenerated in Alzheimer's disease patients, or the substantia nigra pars compacta which is found to be degenerated in Parkinson's disease patients. Particularly preferred neural tissue is obtained from ventricular tissue that is found lining CNS ventricles and includes the subependyma. The term "ventricle" refers to any cavity or passageway within the CNS through which cerebral spinal fluid flows. Thus, the term not only encompasses the lateral, third, and fourth ventricles, but also encompasses the central canal, cerebral aqueduct, and other CNS cavities.

Cells can be obtained from donor tissue (e.g., neural tissue) by dissociation of individual cells from the connecting extracellular matrix of the tissue. The donor tissue may be tissue from any cell or organ that comprise neural tissue listed in this application including, at least, LV cells and hippcampus cells. Tissue from a particular neural region is removed from the brain using a sterile procedure, and the cells are dissociated using any method known in the art including treatment with enzymes such as trypsin, collagenase and the like, or by using physical methods of dissociation such as with a blunt instrument. Dissociation of fetal cells can be carried out in tissue culture medium, while a preferable medium for dissociation of juvenile and adult cells is low $Ca.^{2+}$ artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM. Dissociated cells are centrifuged at low speed, between 200 and 2000 rpm, usually between 400 and 800 rpm, and then resuspended in culture medium. The cells can be cultured in suspension or on a fixed substrate.

Methods for culturing neural cells are well known. See, U.S. Pat. Nos. 5,980,885, 5,851,832, 5,753,506, 5,750376, 5,654,183, 5,589,376, 5,981,165, and 5,411,883, all incorporated herein by reference. A preferred embodiment for proliferation of stem cells is to use a defined, serum-free culture medium (e.g., Complete Medium), as serum tends to induce differentiation and contains unknown components (i.e. is undefined). A defined culture medium is also preferred if the cells are to be used for transplantation purposes. A particularly preferable culture medium is a defined culture medium comprising a mixture of DMEM, F12, and a defined hormone and salt mixture. Conditions for culturing should be close to physiological conditions. The pH of the culture medium should be close to physiological pH, preferably between pH 6–8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C.

The culture medium is supplemented with at least one neurogenesis modulating agent of the invention. This ability of the neurogenesis modulating agent to enhance the proliferation of stem cells is invaluable when stem cells are to be harvested for later transplantation back into a patient, thereby making the initial surgery 1) less traumatic because less tissue would have to be removed 2) more efficient because a greater yield of stem cells per surgery would proliferate in vitro; and 3) safer because of reduced chance for mutation and neoplastic transformation with reduced culture time. Optionally, the patient's stem cells, once they have proliferated in vitro, could also be genetically modified in vitro using the techniques described below.

After proliferation Stem cell progeny can be cryopreserved until they are needed by any method known in the art. In a preferred embodiment of the invention, the cells are derived from the lateral ventricle wall region of the brain. In another preferred embodiment of the invention, the cells are derived from the CNS but not from the hippocampus.

Cellular Differentiation:

Included in the invention are methods of using the disclosed neurogenesis modulating agents to increase or maintain cell (e.g., stem cell or progenitor cell) proliferation in vitro and obtain large numbers of differentiated cells. Differentiation of the cells can be induced by any method known in the art. In a preferred method, differentiation is induced by contacting the cell with a neurogenesis modulating agent of the invention that activates the cascade of biological events that lead to growth and differentiation. As disclosed in this invention, these events include elevation of intracellular cAMP and $Ca^{2+}$.

Cellular differentiation may be monitored by using antibodies to antigens specific for neurons, astrocytes, or oligodendrocytes can be determined by immunocytochemistry techniques well known in the art. Many neuron specific markers are known. In particular, cellular markers for neurons include NSE, NF, beta-tub, MAP-2; and for glia, GFAP (an identifier of astrocytes), galactocerebroside (GalC) (a myelin glycolipid identifier of oligodendrocytes), and the like.

Differentiation may also be monitored by in situ hybridization histochemistry that can also be performed, using cDNA or RNA probes specific for peptide neurotransmitter or neurotransmitter synthesizing enzyme mRNAs. These techniques can be combined with immunocytochemical methods to enhance the identification of specific phenotypes. If necessary, additional analysis may be performed by Western and Northern blot procedures.

A preferred method for the identification of neurons uses immunocytochemistry to detect immunoreactivity for NSE, NF, NeuN, and the neuron specific protein, tau-1. Because these markers are highly reliable, they will continue to be useful for the primary identification of neurons, however neurons can also be identified based on their specific neurotransmitter phenotype as previously described. Type I astrocytes, which are differentiated glial cells that have a flat, protoplasmic/fibroblast-like morphology, are preferably identified by their immunoreactivity for GFAP but not A2B5. Type II astrocytes, which are differentiated glial cells that display a stellate process-bearing morphology, are preferably identified using immunocytochemistry by their phenotype GFAP(+), A2B5(+) phenotype.

Administration of Cells Treated with a Method of the Invention:

Following in vitro expansion and neurogenesis using a method of the invention (see, Example section for a detail description of these methods), the cells of the invention can be administered to any animal with abnormal neurological or neurodegenerative symptoms obtained in any manner, including those obtained as a result of mechanical, chemical, or electrolytic lesions, as a result of experimental aspiration of neural areas, or as a result of aging processes. Particularly preferable lesions in non-human animal models are obtained with 6-hydroxy-dopamine (6-OHDA), 1-methyl-4-phenyl-1,2,3,6 tetrahydropyridine (MPTP), ibotenic acid and the like.

The instant invention allows the use of cells (e.g., stem cells or progenitor cells) that are xenogeneic to the host. The methods of the invention are applied to these cells (as shown in the Examples) to expand the total number or total percent of neuronal stem cells in culture before use. Since the CNS is a somewhat immunoprivileged site, the immune response is significantly less to xenografts, than elsewhere in the body. In general, however, in order for xenografts to be successful it is preferred that some method of reducing or eliminating the immune response to the implanted tissue be employed. Thus recipients will often be immunosuppressed, either through the use of immunosuppressive drugs such as cyclosporin, or through local immunosuppression strategies employing locally applied immunosuppressants. Local immunosuppression is disclosed by Gruber, Transplantation 54:1–11 (1992). Rossini, U.S. Pat. No. 5,026,365, discloses encapsulation methods suitable for local immunosuppression.

Grafting of cells prepared from tissue that is allogeneic to that of the recipient will most often employ tissue typing in an effort to most closely match the histocompatibility type of the recipient. Donor cell age as well as age of the recipient have been demonstrated to be important factors in improving the probability of neuronal graft survival. In some instances, it may be possible to prepare cells from the recipient's own nervous system (e.g., in the case of tumor removal biopsies, etc.). In such instances the cells may be generated from dissociated tissue and proliferated in vitro using the methods described above. Upon suitable expansion of cell numbers, the cells may be harvested, genetically modified if necessary, and readied for direct injection into the recipient's CNS.

Transplantation can be done bilaterally, or, in the case of a patient suffering from Parkinson's disease, contralateral to the most affected side.

Surgery may be used to deliver cells throughout any affected neural area, in particular, to the basal ganglia, and preferably to the caudate and putamen, the nucleus basalis or the substantia nigra. Cells are administered to the particular region using any method that maintains the integrity of surrounding areas of the brain, preferably by injection cannula. Injection methods exemplified by those used by Duncan et al. J. Neurocytology, 17:351–361 (1988), and scaled up and modified for use in humans are preferred.

Although solid tissue fragments and cell suspensions of neural tissue are immunogenic as a whole, it could be possible that individual cell types within the graft are themselves immunogenic to a lesser degree. For example, Bartlett et al. (Prog. Brain Res. 82: 153–160 (1990)) have abrogated neural allograft rejection by pre-selecting a subpopulation of embryonic neuroepithelial cells for grafting by the use of immunobead separation on the basis of MHC expression. Thus, another approach is provided to reduce the chances of allo- and xenograft rejection by the recipient without the use of immunosuppression techniques.

Cells when administered to the particular neural region preferably form a neural graft, wherein the neuronal cells form normal neuronal or synaptic connections with neighboring neurons, and maintain contact with transplanted or existing glial cells which may form myelin sheaths around the neurons' axons, and provide a trophic influence for the neurons. As these transplanted cells form connections, they re-establish the neuronal networks which have been damaged due to disease and aging.

Survival of the graft in the living host can be examined using various non-invasive scans such as computerized axial tomography (CAT scan or CT scan), nuclear magnetic resonance or magnetic resonance imaging (NMR or MRI) or more preferably positron emission tomography (PET) scans. Post-mortem examination of graft survival can be done by removing the neural tissue, and examining the affected region macroscopically, or more preferably using microscopy. Cells can be stained with any stains visible under light or electron microscopic conditions, more particularly with stains that are specific for neurons and glia. Particularly useful are monoclonal antibodies that identify neuronal cell surface markers such as the M6 antibody, which identifies mouse neurons. Most preferable are antibodies that identify any neurotransmitters, particularly those directed to GABA, TH, ChAT, and substance P, and to enzymes involved in the synthesis of neurotransmitters, in particular, GAD. Transplanted cells can also be identified by prior incorporation of tracer dyes such as rhodamine- or fluorescein-labeled microspheres, fast blue, bisbenzamide or retrovirally introduced histochemical markers such as the lacZ gene, which produces beta galactosidase.

Functional integration of the graft into the host's neural tissue can be assessed by examining the effectiveness of grafts on restoring various functions, including but not limited to tests for endocrine, motor, cognitive and sensory functions. Motor tests that can be used include those that quantitate rotational movement away from the degenerated side of the brain, and those that quantitate slowness of movement, balance, coordination, akinesia or lack of movement, rigidity and tremors. Cognitive tests include various tests of ability to perform everyday tasks, as well as various memory tests, including maze performance.

Cells (e.g., stem cells or progenitor cells) can be produced and transplanted using the above procedures to treat demyelination diseases as described in detail herein. Human demyelinating diseases for which the cells of the present invention may provide treatment include disseminated perivenous encephalomyelitis, MS (Charcot and Marburg types), neuromyelitis optica, concentric sclerosis, acute, disseminated encephalomyelitides, post encephalomyelitis, postvaccinal encephalomyelitis, acute hemorrhagic leukoencephalopathy, progressive multifocal leukoencephalopathy, idiopathic polyneuritis, diphtheric neuropathy, Pelizaeus-Merzbacher disease, neuromyelitis optica, diffuse cerebral sclerosis, central pontine myelinosis, spongiform leukodystrophy, and leukodystrophy (Alexander type).

Standard stereotactic neurosurgical methods may be used to inject cell suspensions both into the brain and spinal cord. Generally, the cells can be obtained from any of the sources discussed above. However, in the case of demyelinating diseases with a genetic basis directly affecting the ability of the myelin forming cell to myelinate axons, allogeneic tissue would be a preferred source of the cells as autologous tissue (i.e. the recipient's cells) would generally not be useful unless the cells have been modified in some way to insure the lesion will not continue (e.g. genetically modifying the cells to cure the demyelination lesion).

Oligodendrocytes derived from cells proliferated and differentiated in vitro may be injected into demyelinated target areas in the recipient. Appropriate amounts of type I astrocytes may also be injected. Type I astrocytes are known to secrete PDGF which promotes both migration and cell division of oligodendrocytes (see, e.g., Nobel et al., Nature 333:560–652 (1988); Richardson et al., Cell, 53:309–319 (1988)).

A preferred treatment of demyelination disease uses undifferentiated cells (e.g., stem cells or progenitor cells). Neurospheres grown using a method of the invention can be dissociated to obtain individual cells that are then placed in injection medium and injected directly into the demyelinated target region. The cells differentiate in vivo. Astrocytes can promote remyelination in various paradigms. Therefore, in instances where oligodendrocyte proliferation is important, the ability of precursor cells to give rise to type I astrocytes may be useful. In other situations, PDGF may be applied topically during the transplantation as well as with repeated doses to the implant site thereafter.

Any suitable method for the implantation of cells near to the demyelinated targets may be used so that the cells can become associated with the demyelinated axons. Glial cells are motile and are known to migrate to, along, and across their neuronal targets thereby allowing the spacing of injections. Remyelination by the injection of cells is a useful therapeutic in a wide range of demyelinating conditions. It should also be borne in mind that in some circumstances remyelination by cells will not result in permanent remyelination, and repeated injections or surgeries will be required. Such therapeutic approaches offer advantage over leaving the condition untreated and may spare the recipient's life.

The term injection, throughout this application, encompasses all forms of injection known in the art and at least the more commonly described injection methods such as subcutaneous, intraperitoneal, intramuscular, intracerebroventricular, intraparenchymal, intrathecal, and intracranial injection. Where administration is by means other than injection, all known means are contemplated including administration by through the buccal, nasal, pulmonary or rectal mucosa. Commonly known delivery systems include administration by peptide fusion to enhance uptake or by via micelle or liposome delivery systems.

The methods of the invention may be tested on animal models of neurological diseases. Many such models exist. For example, they are listed in Alan A Boulton, Glen B Baker, Roger F Butterworth "Animal Models of Neurological Disease" Humana Press (1992) and Alan A Boulton, Glen B Baker, Roger F Butterworth "Animal Models of Neurological Disease II" Blackwell Publishing (2000). Also, mouse models for the following diseases may be purchased by a commercial supplier such as the Jackson Laboratory: Alzheimer's disease, Amyotrophic Lateral Sclerosis (ALS), Angelman syndrome, astrocyte defects, ataxia (movement) defects, behavioral and learning defects, cerebellar defects, channel and transporter defects, defects in circadian rhythms, cortical defects, epilepsy, fragile X mental retardation syndrome, Huntington's disease, metabolic defects, myelination defects, neural tube defects, neurodegeneration, neurodevelopmental defects, neuromuscular defects, neuroscience mutagenesis facility strain, neurotransmitter receptor and synaptic vesicle defects, neurotrophic factor defects, Parkinson's disease, receptor defects, response to catecholamines, tremor, tremor defects, and vestibular and hearing defects. (See, e.g., hypertext transfer protocol:// jaxmicejax.org/jaxmicedb/html/sbmodel_13.shtml; over 100 strains of mouse models of neurological diseases are listed in hypertext transfer protocol://jaxmicejax.org/ jaxmicedb/html/model_13.shtml). Rat models of neurological diseases are numerous and may be found, for example, in recent reviews (e.g., Cenci, Whishaw and Schallert, Nat Rev Neurosci. 2002 July; 3(7):574–9). One of skill in the art, reading this disclosure, would be able to use the results of this disclosure to design animal testing models to determine efficacy in vivo. See, also, Example 13. Other animal models include strains that contain the same mutations as the strains described above but in a different genetic background.

Another example, the neurogenesis modulating agents of this disclosure may be tested in the following animals models of CNS disease/disorders/trauma to demonstrate recovery. Models of epilepsy include at least electroshock-induced seizures (Billington A et al., Neuroreport 2000 Nov. 27; 11(17):3817–22), pentylene tetrazol (Gamaniel K et al., Prostaglandins Leukot Essent Fatty Acids 1989 February; 35(2):63–8) or kainic acid (Riban V et al, Neuroscience 2002;112(1):101–11) induced seizures. Models of psychosis/schizophrenia include, at least, amphetamine-induced stereotypies/locomotion (Borison RL & Diamond BI, Biol Psychiatry 1978 April; 13(2):217–25), MK-801 induced stereotypies (Tiedtke et al., J Neural Transm Gen Sect 1990;81(3):173–82), MAM (methyl azoxy methanol-induced (Fiore M et al., Neuropharmacology 1999 June; 38(6):857–69; Talamini LM et al., Brain Res 1999 Nov. 13; 847(1):105–20) or reeler model (Ballmaier M et al., Eur J Neurosci 2002 April; 15(17):1197–205). Models of Parkinson's disease include, at least, MPTP (Schmidt & Ferger, J Neural Transm 2001;108(11):1263–82), 6-OH dopamine (O'Dell & Marshall, Neuroreport 1996 Nov. 4; 7(15–17): 2457–61) induced degeneration. Models of Alzheimer's disease include, at least, fimbria fornix lesion model (Krugel et al., Int J Dev Neurosci 2001 June; 19(3):263–77), basal forebrain lesion model (Moyse E et al., Brain Res 1993 Apr. 2; 607(1–2):154–60). Models of stroke include, at least, focal ischemia (Schwartz DA et al., Brain Res Mol Brain Res 2002 May 30; 101(1–2):12–22); global ischemia (2- or 4-vessel occlusion) (Roof RL et al., Stroke 2001 November; 32(11):2648–57; Yagita Y et al., Stroke 2001 August; 32(8): 1890–6).

In addition, models of multiple sclerosis include, at least, myelin oligodendrocyte glycoprotein -induced experimental autoimmune encephalomyelitis (Slavin A et al., Autoimmunity 1998;28(2):109–20). Models of amyotrophic lateral sclerosis include, at least pmn mouse model (Kennel P et al., J Neurol Sci 2000 Nov. 1; 180(1–2):55–61). Models of anxiety include, at least, elevated plus-maze test (Holmes A et al., Behav Neurosci 2001 October; 115(5):112944), marble burying test (Broekkamp et al., Eur J Pharmacol 1986 Jul. 31; 126(3):223–9), open field test (Pelleymounter et al., J Pharmacol Exp Ther 2002 July; 302(1):145–52).

Models of depression include, at least learned helplessness test, forced swim test (Shirayama Y et al., J Neurosci 2002 Apr. 15; 22(8):3251–61), bulbectomy (O'Connor et al., Prog Neuropsychopharmacol Biol Psychiatry 1988;12(1):41–51). Model for learning/memory include, at least, Morris water maze test (Schenk F & Morris R G, Exp Brain Res 1985;58 (1):11–28). Models for Huntington's disease include, at least, quinolinic acid injection (Marco S et al., J Neurobiol 2002 March; 50(4):323–32), transgenics/knock-ins (reviewed in Menalled L B and Chesselet M F, Trends Pharmacol Sci. 2002 January; 23(1):32–9). Models of aged animal include, at least, the use of old animals such as old mice and old rats.

Other features of the invention will become apparent in the course of the following description of exemplary embodiments that are given for illustration of the invention and are not intended to be limiting thereof. All references, patents, and patent applications cited are hereby incorporated by reference in their entirety.

EXAMPLES

Unless noted otherwise, all experiments were performed using standard molecular biology techniques which are also described in co pending U.S. application Ser. No. 10/429,062 filed May 2, 2003, incorporated herein by reference.

Example 1

Reagents

Chemicals for dissociation of tissue included trypsin, hyaluronidase, and DNase (all purchased from SIGMA). Medium (DMEM 4.5 mg/ml glucose, and DMEM/F12), B27 supplement, and trypsin/EDTA were purchased from GIBCO. All plastic ware was purchased from CorningCostar. EGF for cell cultures was purchased from BD Biosciences, and the ATP-SL kit was purchased from BioThema.

For the test substances, the library was purchased from Phoenix pharmaceuticals Inc., USA, variety Pack Peptide Library (#L-001). Compounds purchased from Sigma-Aldrich included forskolin (#F6886), rolipram (#R6520), n-6, 2-o-dibutyryladenosine (#D0260), cholera toxin (#C8052), MECA (#A024), HE-NECA (#H8034), nor-Binaltorphimine (#N1771), and adrenocorticotropic hormone (#A0298).

Example 2

Mouse Neurosphere Cultures

The anterior lateral wall of the lateral ventricle of 5–6 week old mice was enzymatically dissociated in 0.8 mg/ml hyaluronidase and 0.5 mg/ml trypsin in DMEM containing 4.5 mg/ml glucose and 80 units/ml DNase at 37° C. for 20 minutes. The cells were gently triturated and mixed with Neurosphere medium (DMEM/F12, B27 supplement, 12.5 mM HEPES pH7.4), 100 units/ml penicillin and 100 $\mu$/ml streptomycin. After passing through a 70 $\mu$m strainer, the cells were pelleted at 200×g for 4 minutes. The supernatant was subsequently removed and the cells were resuspended in Neurosphere medium supplemented with 3 nM EGF. Cells were plated out in culture dishes and incubated at 37° C. Neurospheres were ready to be split at approximately 7 days after plating.

To split neurosphere cultures, neurospheres were collected by centrifugation at 200×g for 4 minutes. The neurospheres were resuspended in 0.5 ml trypsin/EDTA in HBSS (1×), incubated at 37° C. for 2 minutes, and triturated gently to aid dissociation. Following another 3 minutes incubation at 37° C. and trituration, the cells were pelleted at 220×g for 4 minutes. Cells were resuspended in freshly prepared Neurosphere medium supplemented with 3 nM EGF and 1 nM bFGF. Cells were plated out and incubated at 37° C.

Example 3

ATP-Assay

To determine proliferation, neurospheres were split and seeded in Neurosphere medium as single cells in 96-well plates, at 10,000 cells/well. The following experiment was performed in sets of four parallel experiments (i.e., performed in quadruplicate) such that the cells may be used for different assays. Substances to be tested were added and cells were incubated at 37° C. for 4 days. Cells were lysed with 0.1 % Triton-X100 in Tris-EDTA buffer. Intracellular ATP was measured using an ATP-SL kit according to the manufacturer's instructions (BioThema, Sweden). Intracellular ATP was shown to correlate with cell number. For each experiment, wells were visually examined for signs of neurogenesis and counted to confirm the results of the assay. Results were repeatable and statistically significant.

Example 4 cAMP Detection Method

For testing elevations in cAMP levels, the HitHunter EFC Cyclic AMP Chemiluminescence Assay Kit was used (DiscoveRx,USA), as purchased from Applied Biosystems. Cells were dissociated as described earlier. Cells were then seeded as non-adherent neurosphere culture at 30,000 cells/well to permit reproducible measurements of cAMP levels. The cells were allowed to rest for 2 hours prior to addition of the test substances. Following the resting period, 1 mM IBMX (3 isobutyl-1-methil-xanthine, Sigma) was added to each well and incubated for 10 minutes in 37° C., according to instructions of the manufacturer. Test substances were incubated for 20 minutes at 37° C. before the cells were lysed and cAMP was measured. Each substance was tested in 3 doses (100, 10, or 1 nM), with each dose tested in quadruplicate. cAMP was measured according to kit instructions, and results were represented as pmol/well. Student's t-test was used to calculate for significance.

Example 5

$Ca^{2+}$ Measurement Using NFAT Response Element Reporter System

Elevations in $Ca^{2+}$ levels were determined using a vector construct that coded for the nuclear factor of activated T cells (NFAT) response element coupled to a luciferase reporter. NFAT was previously reported to be regulated in a $Ca^{2+}$ dependent manner (Rao et al., 1997). The luciferase signal was detected with the Staedy-Glo kit (Promega). After dissociating the cells (as described above), 4–6×10$^6$ cells were centrifuged at 250×g for 4 minutes. The supernatant was discarded and the cells were resuspended in 100 $\mu$l Nucleofector™ Solution (Amaxa GmbH) and 10 $\mu$g NFAT-Luc vector DNA per 10$^6$ cells. The suspension was transferred to a cuvette and electroporated. The transfected cells were seeded at 50,000 cells/well as non-adherent neurosphere cultures. The cells were allowed to rest over night before being contacted with the test substances. Each substance was tested in 34 doses (100, 15, 1.5, or 0.15 nM), with each dose tested in quadruplicate. Luciferace was measured according to the manufacturer's instructions at 18–24 hours post-induction. Results were represented as fold induction compared to untreated control. Student's t-test was used to calculate significance compared to untreated control.

Example 6 cDNA Libraries and Expression Analysis

For the LVW cDNA library, RNA was isolated from the anterior lateral ventricle of adult mice (C57 black). An oligo dT-primed cDNA library was generated using standard procedures (Superscript One-Step RT-PCR with platinum Taq, Invitrogen), and then subjected to sequence analysis (9,000 sequences). For the Neurosphere cDNA Library, RNA was isolated from second generation neurospheres derived from the anterior lateral ventricle wall of adult mice (C57 black), and expanded using the growth factors EGF and FGF2. An oligo-dT-primed normalized cDNA library was generated using standard procedures (Superscript One-Step RT-PCR with platinum Taq, Invitrogen), and then subjected to sequence analysis (12,500 sequences).

Adult Human Neural Stem Cell (aHNSC) Cultures

A biopsy from the anterior lateral wall of the lateral ventricle was taken from an adult human patient and enzymatically dissociated in PDD (Papain 2.5 U/ml; Dispase 1 U/ml; DNase I 250 U/ml) in DMEM containing 4.5 mg/ml glucose and 37° C. for 20 min. The cells were gently triturated and mixed with three volumes of DMEM/F12; 10% fetal bovine serum (FBS). The cells were pelleted at 250×g for 5 min. The supernatant was subsequently removed and the cells resuspended in DMEM F12 with 10% FBS, plated out on fibronectin coated culture dishes, and incubated at 37° C. in 5% $CO_2$. The following day the expansion of the culture was initiated by change of media to aHNSC culture media (DMEM/F12; BIT 9500; EGF 20 ng/ml; FGF2 20 ng/ml). The aHNSC were split using trypsin and EDTA under standard conditions. FBS was subsequently added to inhibit the reaction and the cells collected by centrifugation at 250×g for 5 min. The aHNSC were replated in aHNSC culture media.

RT-PCR

The cultures aHNSC were harvested and total RNA was extracted with an RNeasy mini kit (Qiagen) according to the manual. The primer pairs for the following genes (see table below) were designed and synthesized to identify their presence in aHNSC.

| Gene name | GenBank Acc. No. | Primers | |
|---|---|---|---|
| ADORA2A | NM_000675 | 5'-CAATGTGCTGGTGTGCTGG | (SEQ ID NO:43) |
|  |  | 3'-TAGACACCCAGCATGAGCAG | (SEQ ID NO:44) |
| EDNRA | NM_001957 | 5'-CAGGATCATTTACCAGAAC | (SEQ ID NO:45) |
|  |  | 3'-GACGCTGCTTAAGATGTTC | (SEQ ID NO:46) |
| CALCRL | NM_005795 | 5'-AGAGCCTAAGTTGCCAAAGG | (SEQ ID NO:47) |
|  |  | 3'-GAATCAGCACAAATTCAATG | (SEQ ID NO:48) |
| MC1R | NM_002386 | 5'-GAACCGGAACCTGCACTC | (SEQ ID NO:49) |
|  |  | 3'-TGCCCAGCAGGATGGTGAG | (SEQ ID NO:50) |
| MC5R | NM_005913 | 5'-GAGAACATCTTGGTCATAGG | (SEQ ID NO:51) |
|  |  | 3'-AGCATTAAAGTGAGATGAAG | (SEQ ID NO:52) |
| VIPR1 | NM_004624 | 5'-GCTACACCATTGGCTACGG | (SEQ ID NO:53) |
|  |  | 3'-GACTGCTGTCACTCTTCCTG | (SEQ ID NO:54) |
| VIPR2 | NM_003382 | 5'-GATGTCTCTTGCAACAGGAAG | (SEQ ID NO:55) |
|  |  | 3'-GCAAACACCATGTAGTGGAC | (SEQ ID NO:56) |
| SSTR1 | NM_001049 | 5'-GGGAACTCTATGGTCATCTACGTGA | (SEQ ID NO:57) |
|  |  | 3'-GAAATGTGTACAACACGAAGCCC | (SEQ ID NO:58) |
| SSTR2 | NM_001050 | 5'-GGCAACACACTTGTCATTTATGTCA | (SEQ ID NO:59) |
|  |  | 3'-AGGTAGCAAAGACAGATGATGGTGA | (SEQ ID NO:60) |
| ADCYAP1R1 | NM_001118 | 5'-TACTTTGATGACACAGGCTGCT | (SEQ ID NO:61) |
|  |  | 3'-AGTACAGCCACCACAAAGCCCT | (SEQ ID NO:62) |

One step RT-PCR (Life Technologies) was performed with the primers to detect the mRNA of the genes of interest. As a positive control, primers for the gene Flt-1 were used. The gene Flt-1 is known to be expressed in the aHNSC. As a negative control primers for the Flt-1 gene were used and Taq enzyme alone was added to ensure that the material had no genomic contamination. The PCR products were run on an 1.5% agarose gel containing ethidium bromide. The bands of the correct size were cut out and cleaned with Qiagen's gel extraction kit. To increase the amount of material for sequencing, the bands were amplified again with their corresponding primers and thereafter sequenced to confirm their identity.

Example 7

CREB Phosphorylation Assays

Briefly, NSC were split into a single cell suspension as described above. The suspension was plated in 6-well plates coated with poly-D-lysine at a density of $10^6$ cells/well. Cells were incubated in media supplemented with 1% of fetal calf serum (FBS) and allowed to adhere overnight. The following morning, the media was carefully replaced with fresh DMEM/F12, and 100 nM PACAP or 100 nM cholera toxin was added to the medium. CREB phosphorylation was determined at 15 minutes and 4 hours time points after PACAP treatment, and at 15 minutes, 4 hours, 6 hours, and 8 hours time points after cholera toxin treatment. Cell lysates were collected and Western blot analysis was performed following standard procedures (Patrone et al., 1999). The specific anti-phospho-CREB antibody (1:1000 dilution; Upstate Biotechnology) was utilized.

Example 8

Flow Cytometry Analysis

Cells were split into as single cell suspensions, as described above. Cells were plated in 6-well-plates coated with poly-D-lysine at a density of $10^6$ cells/well. Following this, 1% FBS was added to the media, and the cells were allowed to adhere over night. The following morning, the media was carefully replaced with fresh DMEM/F12, and the test substance was added to a predetermined final concentration. Cells were grown for 4 days in the presence of the substance. A complete media change was performed halfway through the incubation period. Cells were harvested by incubation with trypsin/EDTA for 5 minutes at 37° C. and gentle flushing with a 1000 µl pipette. Cells were flushed and centrifuged with 500 µl media at 250×g for 4 minutes.

Following this, $2 \times 10^5$ cells were transferred into minicentrifuge tubes and pelleted. The pellet was carefully resuspended in 50 µl fixation buffer (Caltag) and incubated for 15 minutes at room temperature. Next, 450 µl PBS was added to the tube. The cells were centrifuged at 200×g for 5 minutes, and the supernatant was removed. Cells were resuspended in 100 µl permeabilization buffer (Caltag) and primary antibody was added (Doublecortin 1:200, Santa Cruz) for 20 minutes at room temperature. Cells were washed as above and resuspended in secondary antibody diluted in 100 µl PBS (FITC anti-goat IgG, 1:500, Vector Laboratories). Cells were incubated in the dark for 20 minutes at room temperature. Thereafter, the cells were washed as above, resuspended in 100 µl PBS, and transferred to tubes suitable for FACS analysis.

For FACS analysis, cells were analyzed on a FACSCalibur (Becton Dickinson). Fluorescence signals from individual cells were excited by an argon ion laser at 488 nm, and the resulting fluorescence emissions from each cell was collected using bandpass filters set at 530±30. Cell Quest Pro acquisition and analysis software was used to collect the fluorescence signal intensities, as well as forward and side scattering properties of the cells. The software was also used to set logical electronic gating parameters designed to differentiate between alive versus dead cells, as well as between positive and negative cells. A total of 10,000 cells per sample were analyzed.

Example 9 cAMP Levels Correlate to Neuronal Stem Cell Proliferation

The aim of this investigation was to determine if cAMP and $Ca^{2+}$ are important regulators of proliferation in adult neuronal stem cells. The experiments analyzed a large number of test substances, most of which regulate cAMP and/or $Ca^{2+}$ via GPCRs. The results of these experiments indicated that: 1) cAMP levels were correlated with mouse neural stem cells proliferation; 2) intracellular $Ca^{2+}$ stimulation was correlated with mouse neural stem cell proliferation; 3) adult mouse stem cells retain their potential to differentiate towards any neuronal cell (phenotype); and 4) adult mouse and human neural stem cells showed similar, reproducible responses to cAMP stimulation.

To determine if cAMP pathways cause proliferation, adult neural stem cells were stimulated in vitro by incubation with a diverse set of cAMP cellular activators (Table 1, column 1). The results of these studies clearly demonstrate that induction of cAMP in neural stem cells leads to cell proliferation (Table 1, columns 2–6). Adult mouse stem cells grown in vitro were induced to proliferate following treatment with several compounds belonging to a chemical library of GPCR ligands (Example 1; Table 2, column 1). The cAMP levels were measured 15 minutes after the different treatments (Table 2, columns 5–6). ATP levels, a measure of cell number, were measured following 4 days of treatment (Table 2, columns 3–4). The results indicate a clear correlation between proliferation (ATP levels) and cAMP induction in all the substances analyzed. The GPCRs for the ligands listed in Tables 1 and 2, are shown in Table 3, columns 1–3. Expression data for the GPCRs was obtained from mouse neurospheres and lateral ventricle cDNA libraries (Table 3, columns 4–5).

TABLE 1

Proliferation (ATP levels) and cAMP levels are closely correlated in mouse adult neural stem cells

| Substance | Conc. (nMolar) | ATP (nM ATP/well) | Fold Induction ATP | cAMP (pmol/well) | Fold Induction cAMP |
|---|---|---|---|---|---|
| Vehicle | | 9.3 ± 0.6 | 1.0 | 0.02 ± 0.01 | |
| Forskolin | 1000 | 10.4 ± 2.4 | 1.1 | 0.07 ± 0.01 | 3.1** |
| Rolipram | 100 | 10.4 ± 0.4 | 1.1* | 0.09 ± 0.03 | 3.8* |
| N-6, 2-O-Dibutyryl-adenosine | 100 | 13.9 ± 1.1 | 1.5** | 0.10 ± 0.01 | 4.5** |
| Cholera toxin | 100 | 12.9 ± 1.6 | 1.4* | 0.07 ± 0.01 | 3.1*** (10 nM) |

Table 1 shows ATP levels, reflecting cell number, and cAMP levels, following adult neutral stem cell treatment with cAMP chemical activators. Test substances were added to adult mouse stem cell cultures at the indicated doses, and after 15 minutes, cAMP levels were measured.

ATP levels were measured after 4 days in culture.

Fold induction was determined by comparison to vehicle treated cells.

Data was represented as the mean ± SD value of quadruplicate tests in a typical experiment. The representative values were calculated based on two seperate experiments.

*$P < 0.05$;

**$P < 0.005$;

***$P < 0.001$ (Student's test);

n.s. = non significant.

TABLE 2

GPCR ligands that stimulate proliferation (ATP levels) and cAMP activation
in mouse adult neural stem cells. Each agent is a neurogenesis modulating agent.

| Substance | Conc. (nM) | ATP (nM ATP/well) | Fold Induction ATP | cAMP (pmol/well) | Fold Induction cAMP |
|---|---|---|---|---|---|
| Vehicle | | 16.4 ± 1.3 | | 2.23 ± 0.52 | |
| Adrenocorticotropic hormone | 10 | 18.6 ± 1.0 | 1.1* | 6.36 ± 2.58 | 2.8* (100 nM) |
| Vehicle | | 16.4 ± 1.3 | | 1.84 ± 0.53 | |
| Endothelin-1 (human, porcine) | 10 | 41.7 ± 7.2 | 2.5* | 3.64 ± 1.13 | 2.0* |
| Vehicle | | 4.5 ± 0.6 | | 1.84 ± 0.53 | |
| MECA | 100 | 7.4 ± 0.7 | 1.6** | 3.89 ± 1.00 | 2.1* |
| HE-NECA | 1000 | 8.2 ± 1.1 | 1.8** | 3.32 ± 0.28 | 1.8*** (10 nM) |
| Vehicle | | 8.6 ± 1.4 | | 0.13 ± 0.02 | |
| [Cys3,6, Tyr8, Pro9]-Substance P | 100 | 11.2 ± 0.4 | 1.3** | 0.29 ± 10 | 2.2* |
| Vehicle | | 8.6 ± 1.4 | | 0.13 ± 0.02 | |
| [D-Arg0, Hyp3, Ig15, D-Ig17, Oic8]-Bradykinin | 100 | 13.1 ± 2.1 | 1.5* | 0.17 ± 0.02 | 1.3* (10 nM) |
| Vehicle | | 10.3 ± 0.6 | | 0.06 ± 0.01 | |
| Adrenomedullin (human) | 100 | 11.6 ± 0.8 | 1.1* | 0.15 ± 0.3 | 2.5** |
| Vehicle | | 8.8 ± 0.9 | | 0.03 ± 0.01 | |
| [Des-Arg9, Leu8]-Bradykinin | 10 | 9.8 ± 0.4 | 1.1* | 0.09 ± 0.02 | 2.6* (1 nM) |
| [Des-Arg9]-Bradykinin | 1 | 10.4 ± 1.0 | 1.2* | 0.06 ± 0.01 | 1.7*** |
| [D-Pen2-5]-Enkephalin | 10 | 10.7 ± 0.9 | 1.2** | 0.06 ± 0.01 | 1.7* |
| [D-pGlu1,D-Phe2, D-Trp3,6]-LH-RH | 100 | 11.1 ± 0.4 | 1.3*** | 0.07 ± 0.02 | 2.0* (1 nM) |
| Vehicle | | 7.8 ± 2.0 | | 0.21 ± 0.08 | |
| Adrenomedullin (26–52) | 1 | 11.4 ± 0.7 | 1.5** | 0.33 ± 0.07 | 1.6* |
| Adrenomedullin (22–52) | 100 | 12.3 ± 1.1 | 1.6** | 0.34 ± 0.07 | 1.6* |
| α-Neo-Endorphin | 100 | 13.8 ± 2.1 | 1.8** | 0.36 ± 0.09 | 1.7* (1 nM) |
| Vehicle | | 10.3 ± 2.2 | | 0.17 ± 0.04 | |
| β-MSH | 100 | 13.6 ± 1.6 | 1.3* | 0.23 ± 0.02 | 1.3** (10 nM) |
| Vehicle | | 7.8 ± 2.0 | | 2.23 ± 0.52 | |
| α-MSH | 100 | 14.7 ± 3.5 | 1.9*** | 5.82 ± 0.86 | 2.6** (100 nM) |
| Vehicle | | 7.1 ± 0.5 | | 0.17 ± 0.04 | |
| Thyrocalcitonin (Salmon) | 1 | 9.2 ± 0.7 | 1.3* | 0.63 ± 0.23 | 3.8* (1 nM) |
| Vehicle | | 7.1 ± 0.5 | | 0.10 ± 0.02 | |
| Calcitonin (human) | 100 | 9.9 ± 1.6 | 1.4* | 0.35 ± 0.15 | 3.3* |
| CART (61–102) | 100 | 8.3 ± 0.4 | 1.2** | 0.13 ± 0.02 | 1.2* (10 nM) |
| Vehicle | | 8.8 ± 0.9 | | 0.09 ± 0.03 | |
| Cholecystokinin Octapeptide [CCK(26–33)] | 10 | 9.8 ± 0.4 | 1.1* | 0.27 ± 0.06 | 3.1** (100 nM) |
| Vehicle | | 7.6 ± 1.0 | | 0.14 ± 0.02 | |
| DTLET | 10 | 9.2 ± 0.9 | 1.2* | 0.20 ± 0.02 | 1.4* (100 nM) |
| Vehicle | | 7.6 ± 1.0 | | 0.14 ± 0.02 | |
| DDAVP | 100 | 11.5 ± 1.4 | 1.5* | 0.27 ± 0.02 | 1.9*** (10 nM) |
| Vehicle | | 8.5 ± 1.5 | | 0.84 ± 0.11 | |
| Eledoisin | 100 | 10.4 ± 1.1 | 1.2* | 1.0 ± 0.06 | 1.2* (1 nM) |
| Vehicle | | 6.3 ± 0.2 | | 0.57 ± 0.14 | |
| γ-MSH | 10 | 7.4 ± 0.5 | 1.2* | 0.96 ± 0.18 | 1.7* (100 nM) |
| Vehicle | | 8.7 ± 1.5 | | 0.05 ± 0.06 | |
| α-Neurokinin | 100 | 11.0 ± 1.4 | 1.3* | 0.11 ± 0.03 | 2.3* (10 nM) |
| Vehicle | | 9.4 ± 1.4 | | 0.03 ± 0.01 | |
| PACAP-38 | 100 | 26.9 ± 3.7 | 2.9** | 0.13 ± 0.03 | 4.2** |
| Vehicle | | 10.3 ± 2.2 | | 0.17 ± 0.04 | |
| Beta-ANP | 100 | 13.6 ± 2.1 | 1.3* | 070 ± 0.04 | 4.2*** |
| Vehicle | | 6.3 ± 0.2 | | 0.57 ± 0.14 | |
| Galanin (1–13)-Spantide-Amide, M40 | 100 | 7.10 ± 0.5 | 1.1* | 0.82 ± 0.08 | 1.4** (1 nM) |
| Vehicle | | 12.5 ± 1.8 | | 0.07 ± 0.06 | |
| [Sar9, Met (0)11]-Substance P | 100 | 39.7 ± 2.1 | 3.2*** | 0.16 ± 0.05 | 2.2* |
| Vehicle | | 12.5 ± 1.8 | | 0.30 ± 0.08 | |
| Sarafotoxin S6a | 10 | 43.3 ± 4.5 | 3.5*** | 0.41 ± 0.06 | 1.4* |

TABLE 2-continued

GPCR ligands that stimulate proliferation (ATP levels) and cAMP activation in mouse adult neural stem cells. Each agent is a neurogenesis modulating agent.

| Substance | Conc. (nM) | ATP (nM ATP/well) | Fold Induction ATP | cAMP (pmol/well) | Fold Induction cAMP |
|---|---|---|---|---|---|
| Vehicle | | 15.2 ± 3.2 | | 0.07 ± 0.06 | |
| Sarafotoxin S6b | 100 | 43.0 ± 7.8 | 2.8** | 0.43 ± 0.22 | 6.0* |
| Sarafotoxin S6c | 10 | 39.9 ± 6.6 | 2.6** | 0.21 ± 0.03 | 3.0** |
| Vehicle | | 13.5 ± 1.9 | | 0.06 ± 0.01 | |
| [Nle8,18, Tyr34]-Parathyroid Hormone (1–34) Amide (Human) | 1000 | 23.5 ± 2.7 | 1.7** | 0.16 ± 0.05 | 2.6* (10 nM) |
| ACTH (Human) | 1000 | 15.7 ± 1.3 | 1.2* | 0.11 ± 0.02 | 1.8** (100 nM) |
| Glucagon-Like Peptide-1 (7–37) (Human) | 1000 | 18.3 ± 1.4 | 1.3** | 0.08 ± 0.01 | 1.4* (100 nM) |
| Vehicle | | 12.3 ± 1.1 | | 0.14 ± 0.05 | |
| Exendin-3 | 100 | 14.2 ± 1.0 | 1.2* | 0.21 ± 0.03 | 1.5* (10 nM) |
| Vehicle | | 12.3 ± 1.1 | | 0.30 ± 0.08 | |
| Exendin-4 | 1000 | 16.0 ± 2.0 | 1.3* | 0.49 ± 0.04 | 1.6*** (10 nM) |
| Vehicle | | 12.3 ± 1.1 | | 0.20 ± 0.07 | |
| Urotensin II (Globy) | 100 | 14.3 ± 1.1 | 1.2* | 0.50 ± 0.15 | 2.6* (10 nM) |
| Vasoactive Intestinal Peptide (Human, Porcine, Rat) | 1000 | 20.6 ± 1.2 | 1.7*** | 0.39 ± 0.12 | 2.0* (100 nM) |
| Vehicle | | 13.4 ± 1.8 | | 0.97 ± 0.46 | |
| Nor-Binaltorphimine | 0.1 | 19.4 ± 3.2 | 1.4* | 6.10 ± 3.72 | 6.3** (0.01 nM) |
| Vehicle | | 7.8 ± 2.0 | | 0.21 ± 0.08 | |
| Agouti Related Protein (87–132)-Amide (Human) | 10 | 11.2 ± 1.7 | 1.4* | 0.5 ± 0.20 | 2.4* |

Table 2 shows ATP levels, reflecting cell number, and cAMP levels. Test substances were added to adult mouse stem cell cultures at the indicated doses.
After four days, values for ATP and cAMP were assayed.
Fold induction was determined by comparison to vehicle treated cells.
Data was represented as the mean ± SD value of quedruplicate tests in a typical experiment. The representative values were based on two seperate experiments.
*P < 0.05;
**P < 0.005;
***P < 0.001 (Student's test);
n.s. = non significant.
[a]Significant in lower concentration.

TABLE 3

Expression analysis of possible targets for the GPCR ligands listed in Table 2

| Official Name | Locus Link Symbol mouse | Locus Link Symbol Human | Mouse neurosphere Expression | Mouse lateral ventricular wall expression | Human neurosphere Expression |
|---|---|---|---|---|---|
| Adenosine A2a receptor | Adora2a | ADORA2A | YES | YES | n.d. |
| Adenosine A2b receptor | Adora2b | ADORA2B | YES | YES | YES |
| Adenosine A3 receptor | Adora3 | ADORA3 | n.d. | n.d. | n.d. |
| Adenylate cyclase activating polypeptide 1 receptor 1 | Adcyap1r1 | ADCYAP1R1 | YES | YES | YES |
| Adrenomedullin receptor | Admr | ADMR | n.d. | n.d. | YES |
| arginine vasopressin receptor 2 | Avpr2 | AVPR2 | n.d. | n.d. | n.d. |
| Bradykinin receptor, beta 1 | Bdkrb1 | BDKRB1 | n.d. | n.d. | n.d. |
| Bradykinin receptor, beta 2 | Bdkrb2 | BDKRB2 | n.d. | n.d. | n.d. |

TABLE 3-continued

Expression analysis of possible targets for the GPCR ligands listed in Table 2

| Official Name | Locus Link Symbol mouse | Locus Link Symbol Human | Mouse neurosphere Expression | Mouse lateral ventricular wall expression | Human neurosphere Expression |
|---|---|---|---|---|---|
| Calcitonin receptor | Calcr | CALCR | n.d. | n.d. | n.d. |
| Calcitonin receptor-like | Calcrl | CALCRL | n.d. | n.d. | YES |
| Cholecystokinin A receptor | Cckar | CCKAR | n.d. | n.d. | YES |
| Cholecystokinin B receptor | Cckbr | CCKBR | n.d. | n.d. | YES |
| Endothelin receptor type A | Ednra | EDNRA | YES | YES | YES |
| Endothelin receptor type B | Ednrb | EDNRB | YES | YES | n.d. |
| Galanin receptor 1 | Galr1 | GALR1 | n.d. | n.d. | n.d. |
| Galanin receptor 2 | Galr2 | GALR2 | n.d. | n.d. | n.d. |
| Galanin receptor 3 | Galr3 | GALR3 | n.d. | n.d. | n.d. |
| Glucagon-like peptide 1 receptor | Glp1r | GLP1R | n.d. | n.d. | n.d. |
| Gonadotropin releasing hormone receptor | Gnrhr | GNRHR | n.d. | n.d. | n.d. |
| Melanocortin 1 receptor | Mc1r | MC1R | n.d. | n.d. | YES |
| Melanocortin 2 receptor | Mc2r | MC2R | n.d. | n.d. | n.d. |
| Melanocortin 3 receptor | Mc3r | MC3R | n.d. | n.d. | n.d. |
| Melanocortin 4 receptor | Mc4r | MC4R | n.d. | n.d. | n.d. |
| Melanocortin 5 receptor | Mc5r | MC5R | n.d. | n.d. | YES |
| Natriuretic peptide receptor 1 | Npr1 | NPR1 | n.d. | n.d. | n.d. |
| Natriuretic peptide receptor 2 | Npr2 | NPR2 | n.d. | n.d. | n.d. |
| Natriuretic peptide receptor 3 | Npr3 | NPR3 | n.d. | n.d. | n.d. |
| Opioid receptor, delta 1 | Oprd1 | OPRD1 | n.d. | n.d. | n.d. |
| Opioid receptor, kappa 1 | Oprk1 | OPRK1 | n.d. | n.d. | n.d. |
| Tachykinin receptor 1 | Tacr1 | TACR1 | n.d. | n.d. | n.d. |
| Tachykinin receptor 2 | Tacr2 | TACR2 | n.d. | n.d. | n.d. |
| Tachykinin receptor 3 | Tacr3 | TACR3 | n.d. | n.d. | n.d. |
| Vasoactive intestinal peptide receptor 1 | Vipr1 | VIPR1 | YES | YES | YES |
| Vasoactive intestinal peptide receptor 2 | Vipr2 | VIPR2 | YES | YES | YES |
| G protein-coupled receptor 14 | Gpr14 | GPR14 | n.d. | n.d. | n.d. |
| Parathyroid hormone receptor 1 | Pthr1 | PTHR1 | n.d. | n.d. | n.d. |

Table 3 shows that GPCRs were found to be expressed in adult mouse and/or human stem cell cultures. Gene expression in mouse cells or tissue was determined by cDNA library analysis, and human expression using RT-PCR.

A number of compounds that were not previously identified as enhancers of intracellular cAMP were tested for stimulation of neurogenesis. This test was used to determine: 1) if there were additional compounds that could stimulate neurogenesis by any mechanism; and 2) if there were additional compounds that could stimulate neurogenesis by increasing intracellular cAMP. Surprisingly, several of these compounds were found to stimulate neurogenesis even though they were not previously known increase intracellular cAMP levels. The compounds screened included: (Des-Arg9, Leu8)-Bradykinin, (Des-Arg9)-Bradykinin, Alpha-NeoEndorphin, CART (61–102), DTLET, Eledoisin, Urotensin II, [Nle8, 18, Tyr34]-Parathyroid Hormone (1–34) Amide, and [Cys3, 6, Tyr8, Pro9]-Substance P (see Table 2). Our review of the literature showed that these properties (of elevating intracellular cAMP, and inducing neurogenesis) were not previously known.

The experiments were repeated with visual examination of the wells for signs of neurogenesis and to confirm the results of the previous assay. The results were repeatable. The visual analysis confirmed our previous findings and did not reveal anything that would contradict the previous findings.

Example 10

$Ca^{2+}$ Levels Correlate to Neuronal Stem Cell Proliferation

To show that proliferation upon intracellular $Ca^{2+}$ increase in response to GPCR ligands is upregulated in adult mouse stem cells grown in vitro, the cells were treated with a number of test substances (Table 4, column 1). $Ca^{2+}$ was measured via regulation of the nuclear factor of activated T cells gene (NFAT; Example 5). The results show a clear correlation between ATP levels (Table 4, columns 3–4) and NFAT up-regulation (Table 4, columns 5–6). This indicates that $Ca^{2+}$ levels are strongly correlated with neural stem cells proliferation. The GPCRs that trigger $Ca^{2+}$ for the ligands analyzed (Table 5, columns 1–3) were found to be present in the two cDNA libraries analyzed (Example 6; Table 5, columns 4–5). Tables 3 and 5 (columns 6) show GPCRs that were identified in human stem cells material using RT-PCR analysis. This corroborated our findings in adult mouse stem cells, and suggested that the activation of $Ca^{2+}$ is also important for triggering GPCR-mediated proliferation in human stem cells.

TABLE 4

GPCR ligands that regulate NFAT-Luciferace reporter ($Ca^{2+}$) and ATP (proliferation). Each one of these agents is a neurogenesis modulating agent.

| Substance | Conc (nMolar) | ATP (nM ATP/well) | Fold Induction ATP | NFAT Luciferace units | Fold Induction NFAT |
|---|---|---|---|---|---|
| Vehicle | | 9.8 ± 2.1 | | 42.9 ± 7.4 | |
| Amylin Receptor Antagonist/Calcitonin (8–32) | 100 | 15.0 ± 2.2 | 1.5* | 57.3 ± 5.4 | 1.3*** (0.15 nM) |
| Vehicle | | 9.8 ± 1.6 | | 42.9 ± 7.4 | |
| ANP (human) | 10 | 12.7 ± 1.0 | 1.3* | 65.9 ± 8.9 | 1.5* (1.5 nM) |
| Vehicle | | 8.8 ± 0.9 | | 21.1 ± 4.1 | |
| CGRP (8–37) | 100 | 10.4 ± 0.5 | 1.2** | 28.3 ± 1.1 | 1.3** (at 15 nM) |
| Vehicle | | 4.5 ± 0.6 | | 3.4 ± 0.8 | |
| Endothelin-1 (human, Bovine, Canine, Mouse, Porcine, Rat) | 10 | 14.4 ± 2.4 | 3.2* | 8.3 ± 2.5 | 2.4* (0.15 nM) |
| Vehicle | | 6.3 ± 0.2 | | 2.4 ± 1.4 | |
| γ-MSH | 10 | 7.4 ± 0.5 | 1.2* | 4.8 ± 1.5 | 2.0* (1.5 nM) |
| Vehicle | | 7.5 ± 0.6 | | 2.4 ± 1.4 | |
| Growth Hormone Releasing Factor | 10 | 12.6 ± 0.9 | 1.7* | 4.5 ± 0.6 | 1.9** (15 nM) |
| Vehicle | | 8.2 ± 0.8 | | 2.4 ± 1.4 | |
| MGOP 27 | 100 | 10.2 ± 1.2 | 1.2* | 4.0 ± 0.4 | 1.7* (1.5 nM) |
| Vehicle | | 9.4 ± 1.4 | | 3.5 ± 0.9 | |
| PACAP-38 | 10 | 22.0 ± 0.9 | 2.3*** | 6.2 ± 1.6 | 1.7* |
| Vehicle | | 12.5 ± 1.8 | | 1.9 ± 0.5 | |
| Sarafotoxin S6a | 1 | 38.9 ± 3.2 | 3.1*** | 6.3 ± 2.4 | 3.4* |
| Vehicle | | 15.2 ± 3.2 | | 1.9 ± 0.5 | |
| Sarafotoxin S6b | 100 | 43.0 ± 7.8 | 2.8** | 13.4 ± 7.0 | 7.2* |
| Sarafotoxin S6c | 1 | 41.6 ± 4.8 | 2.7*** | 8.3 ± 2.0 | 4.4* |
| Septide | 100 | 25.1 ± 3.1 | 1.7* | 3.7 ± 0.9 | 2.0* |
| Vehicle | | 14.0 ± 1.8 | | 1.9 ± 0.5 | |
| Somatostatin-28 | 10 | 17.1 ± 1.5 | 1.2* | 3.0 ± 0.4 | 1.6* (100 nM) |
| Vehicle | | 9.3 ± 0.06 | | 8.2 ± 0.7 | |
| Cholera toxin from Vibrio Cholerae | 100 | 12.9 ± 1.6 | 1.4* | 11.6 ± 1.0 | 1.4** |
| Vehicle | | 9.8 ± 2.1 | | 5.6 ± 0.5 | |
| Angiotensin II (human synthetic) | | 11.7 ± 0.6 | 1.2* | 12.0 ± 3.7 | 2.1* |
| Vehicle | | 8.8 ± 0.9 | | 5.6 ± 0.5 | |
| [D-Pen2-5]-Enkephalin | 10 | 10.7 ± 0.9 | 1.2* | 10.3 ± 2.1 | 1.8* (100 nM) |

TABLE 4-continued

GPCR ligands that regulate NFAT-Luciferace reporter (Ca$^{2+}$) and ATP (proliferation). Each one of these agents is a neurogenesis modulating agent.

| Substance | Conc (nMolar) | ATP (nM ATP/well) | Fold Induction ATP | NFAT Luciferace units | Fold Induction NFAT |
|---|---|---|---|---|---|
| Vehicle | | 10.3 ± 0.6 | | 5.6 ± 0.5 | |
| Adrenomedullin | 100 | 11.6 ± 0.8 | 1.1* | 12.4 ± 0.9 | 2.2** |
| Vehicle | | 28.1 ± 5.3 | | 8.2 ± 0.7 | |
| Endothelin-1 (human, Porcine,) | 10 | 35.3 ± 3.7 | 1.3* | 13.3 ± 1.3 | 1.6** |

Table 4:
Adult mouse neuronal stem cells were transiently transfected with NFAT-Luciferace construct and induced with test substances at the indicated doses. Cells were analyzed 24 hours after induction.
NFAT-Luciferase activity and ATP was analyzed.
Fold induction was determined by comparison to vehicle treated cells.
The data was represented as the mean ± SD value of quadruplicate tests in a typical experiment.
The representative values were based on two seperate experiments.
*P < 0.05;
**P < 0.005;
***P < .001 (Student's test);
n.s. = non significant.
[a]Significant in lower concentration.

TABLE 5

Expression analysis of targets for the GPCR ligands listed in Table 4

| Official Name | Locus Link Symbol mouse | Locus Link Symbol human | Mouse neurosphere expression | Mouse lateral ventricular wall expression | Human neurosphere expression |
|---|---|---|---|---|---|
| Adenylate cyclase activating polypeptide 1 receptor 1 | Adcyap1r1 | ADCYAP1R1 | YES | YES | YES |
| Angiotensin receptor 1b | Agtr1b | AGTR1 | n.d. | n.d. | n.d. |
| Angiotensin II receptor. type 2 | Agtr2 | AGTR2 | n.d. | n.d. | n.d. |
| Calcitonin receptor | Calcr | CALCR | n.d. | n.d. | n.d. |
| Calcitonin receptor-like | Calcrl | CALCRL | n.d. | n.d. | YES |
| Endothelin receptor type A | Ednra | EDNRA | YES | YES | YES |
| Endothelin receptor type B | Ednrb | EDNRB | YES | YES | n.d. |
| Growth hormone releasing hormone receptor | Ghrhr | GHRHR | n.d. | n.d. | n.d. |
| Melanocortin 1 receptor | Mc1r | MC1R | n.d. | n.d. | YES |
| Melanocortin 3 receptor | Mc3r | MC3R | n.d. | n.d. | n.d. |
| Melanocortin 4 receptor | Mc4r | MC4R | n.d. | n.d. | n.d. |
| Melanocortin 5 receptor | Mc5r | MC5R | n.d. | n.d. | YES |
| Natriuretic peptide receptor 1 | Npr1 | NPR1 | n.d. | n.d. | n.d. |
| Natriuretic peptide receptor 2 | Npr2 | NPR2 | n.d. | n.d. | n.d. |
| Natriuretic peptide receptor 3 | Npr3 | NPR3 | n.d. | n.d. | n.d. |
| Opioid receptor. delta 1 | Oprd1 | OPRD1 | n.d. | n.d. | n.d. |
| Somatostatin receptor 1 | Sstr1 | SSTR1 | YES | YES | YES |
| Somatostatin receptor 2 | Sstr2 | SSTR2 | YES | YES | YES |
| Somatostatin receptor 3 | Sstr3 | SSTR3 | YES | YES | n.d. |

TABLE 5-continued

Expression analysis of targets for the GPCR ligands listed in Table 4

| Official Name | Locus Link Symbol mouse | Locus Link Symbol human | Mouse neurosphere expression | Mouse lateral ventricular wall expression | Human neurosphere expression |
|---|---|---|---|---|---|
| Somatostatin receptor 4 | Sstr4 | SSTR4 | YES | YES | n.d. |
| Somatostatin receptor 5 | Sstr5 | SSTR5 | YES | YES | n.d. |
| Tachykinin receptor 1 | Tacr1 | TACR1 | n.d. | n.d. | n.d. |
| Vasoactive intestinal peptide receptor 1 | Vipr1 | VIPR1 | YES | YES | YES |
| Vasoactive intestinal peptide receptor 2 | Vipr2 | VIPR2 | YES | YES | YES |

Example 11

Human and Mouse Stem Cell Responses to cAMP Stimulation

The experiments described above suggest that intracellular induction of cAMP occurs in proliferative mouse adult neural stem cells. To further investigate the relevance of these 5 findings, the cAMP pathway was studied in human and mouse systems. Since CREB phosphorylation is a well known downstream effector in the cAMP activation pathway (Lonze and Ginty. 2002), the phosphorylation state of this transcription factor was investigated in time course experiments. Two cAMP activators, PACAP and cholera toxin, were utilized (Example 7). PACAP and cholera toxin were added to the adult human and mouse neuronal stem cells. Western blot analysis showed similar up-regulation in mouse as in human neuronal stem cells (FIG. 1). The results clearly demonstrate that the pattern of CREB phosphorylation in both systems is responsive to PACAP and cholera toxin in a reproducible manner (FIG. 1). This suggests that mouse and human stem cells respond in similar ways following cAMP cell induction. GPCRs for which ligands were shown to be proliferative in mouse aNSCs were present also in human aNSCs (Table 3, column 6)

Example 12

Adult Neural Stem Cells Retain their Neuronal Potential Following GPCRs Proliferative Stimuli In order to understand if proliferating adult neural stem cells retained their neuronal potential following GPCR ligand treatment, analysis was performed to determine the expression of the early neuronal marker Doublecortin. Neural stem cells were treated with several GPCRs ligands for 4 days. Flow cytometric analysis was performed on the cells with an antibody against the early neuronal marker Doublecortin. As shown in Table 6, all GPCR ligand-treated cells analyzed continued to express Doublecortin after four days in culture (see also Example 8). This indicated that the ligand-treated adult NSCs were still able to differentiate towards a neuronal phenotype.

TABLE 6

Adult neural stem cells retain their neuronal potential after proliferation with GPCR ligands.

| Substance | Concentration | % Doublecortin-positive cells | Fold Induction |
|---|---|---|---|
| EGF/FGF | 3 nM/1 nM | 2.63 ± 1.86 | 1 |
| Forskolin | 10 μM | 6.3 | 2.5 |
| Cholera toxin from Vibrio Cholerae | 100 nM | 6.7 | 2.6 |
| Endothelin I. human. porcine | 10 nM | 5.0 | 2.0 |
| PACAP-38 | 100 nM | 5.2 | 2.0 |
| (D-Trp7.Ala8.D-Phe10)-α-Melanocyte stimulating hormone F: 6–11/GHRP | 100 nM | 5.3 | 2.1 |
| α-Neurokinin | 100 nM | 4.6 | 1.8 |
| Thyrocalcitonin salmon | 100 nM | 3.9 | 1.5 |
| MECA | 10 μM | 2.2 | 0.9 |
| [Des-Arg9]-Bradykinin | 100 nM | 4.5 | 1.8 |
| Eledoisin | 100 nM | 4.3 | 1.7 |
| γ-Melanocyte stimulating hormone | 100 nM | 4.1 | 1.6 |
| [D-Pen2–5]-Enkephalin | 100 nM | 3.3 | 1.3 |
| α-Neo-Endorphin (Porcine) | 100 nM | 4.0 | 1.6 |
| DTLET | 100 nM | 4.1 | 1.6 |
| [D-Arg0. Hyp3. Ig15. D-Ig17. Oic8]-Bradykinin | 100 nM | 3.6 | 1.4 |

TABLE 6-continued

Adult neural stem cells retain their neuronal potential after proliferation with GPCR ligands.

| Substance | Concentration | % Doublecortin-positive cells | Fold Induction |
|---|---|---|---|
| [D-pGlu1. D-Phe2. D-Trp3.6]-LH-RH | 100 nM | 3.4 | 1.3 |
| Adrenomedullin (Human) | 100 nM | 4.2 | 1.6 |
| Adrenomedullin (22–52) (Human) | 100 nM | 2.0 | 0.8 |
| Agouti Related Protein (87–132)-Amide (Human) | 100 nM | 2.4 | 0.9 |
| Angiotensin II (Human) | 100 nM | 3.1 | 1.2 |
| β-Melanocyte Stimulating Hormone | 100 nM | 4.1 | 1.6 |
| CART (61–102)(Human. Rat) | 100 nM | 4.7 | 1.8 |
| Cholecystokinin Octapeptide [CCK(26–33)] (Non-sulfated) | 100 nM | 3.2 | 1.3 |
| DDAVP (enhances human learning and memory) | 100 nM | 4.6 | 1.8 |
| Sarafotoxin S6a (cardiotoxin isotoxin) | 100 nM | 3.2 | 1.3 |

Table 6:
Cells proliferated by GPCR ligends maintained or increased their potential to mature towards a neuronal phenotype.

The sum of these results and previous studies on PACAP (see, e.g., U.S. Patent Application Ser. No. 60/377,734 filed May 3, 2002; U.S. Patent Application Ser. No. 60/393,264, filed Jul. 2, 2002; U.S. patent application Ser. No. 10/429, 062, filed May 2, 2003; Mercer et al. J. Neurosci. Res. manuscript in press) indicate that compounds (e.g., natural ligands, small chemical entities, affinity proteins, etc.) that increase levels of cAMP or $Ca^{2+}$ can stimulate proliferation of adult neural stem cells in vitro and in vivo. In some cases, this stimulation may be mediated by GPCRs. In addition, cAMP elevation alone (i.e., in a GPCR-independent-manner) can elicit an increase in the proliferation of neural stem cells. This increase was observed with various cAMP activators, including: 1) cAMP-derivatives, such as N-6.2-O-Dibutyryladenosine; 2) inhibitors of cAMP phosphodiesterases, such as 3-Isobutyl-1-Methylxanthine (IBMX) and rolipram; 3) adenylate cyclase activators, such as forskolin; and 4) compounds that elevate ADP-ribosylation of the alpha-subunit of the stimulatory G protein (Gs), such as cholera toxin. Cholera toxin and related compounds are believed to act by reducing GTPase activity and activating the alpha-subunit. This leads to an increase in the activity of adenylate cyclase resulting in increased levels of cAMP. Further, as shown herein, several ligands that act through GPCRs and increase the intracellular $Ca^{2+}$ content are also effective in promoting neurogenesis, including cellular proliferation.

These experiments show that cAMP or $Ca^{2+}$ activation can be used in therapeutic approaches to modulate proliferation, differentiation, survival, or migration of adult neural stem cells/progenitor cells in different physiological or pathological conditions. The various compounds (e.g., GPCRs ligands) described herein may display different cellular specificities and fate profiles, which make them suited for different physiological and pathological conditions. Importantly, adult neural stem cells retained their neuronal potential following GPCR ligand treatment. The sum of these findings implicate a broad range of therapeutic compounds for stimulating neurogenesis through the intracellular elevation of cAMP and/or $Ca^{2+}$.

Example 13

Glp-1 Receptor and Calcitonin Receptor Expression Analysis by RT PCR

Adult mouse brain tissue from lateral ventricular wall and cultured adult mouse neural stem cells (amNSC) were collected and total RNA was extracted with an RNeasy mini kit (Qiagen). The primer pairs for GLP-1 receptor (Glp1r) and Calcitonin receptor (Calcr) were synthesized:

| Gene name | Gene Bank Acc. No. | Primers | |
|---|---|---|---|
| Glp1r | NM_021332 | 5' GTACCACGGTGTCCCTCTCAGA | (SEQ ID NO:65) |
| | | 3'-GGCGGAGAAAGAAAGTGCGT | (SEQ ID NO:66) |
| Calcr | NM_007588 | 5' AACTGCAAAATGCGTACGTTCTTT | (SEQ ID NO:63) |
| | | 3'-GCATCCAGAAGTAGTTGCAAGACAT | (SEQ ID NO:64) |

One step RT-PCR (Platinum Taq Invitrogen) was performed. As a negative control, primers were used and Taq enzyme alone was added to ensure that the material had no genomic contamination. RNA from total mouse brain was used as a positive control since the Glp1r and Calcr genes are known to be expressed elsewhere in the brain. The RNA was DNase treated to eliminate possible DNA contamination. The RT-PCR reactions were run as follows: 1 cycle with incubation at 52° C. for 30 minutes and at 94° C. for 2 minutes; 35 cycles with incubation at 94° C. for 15 seconds, at 56° C. for 30 seconds, and at 72° C. for 30 seconds; 1 cycle with incubation at 72° C. for 7 minutes. The PCR products were run on a 1.5% agarose gel containing ethidium bromide. The PCR product was sequenced and, notably, we found that both Glp1r and Calcr is expressed in mouse brain tissue from lateral ventricular wall. In addition, Glp1r was expressed in cultured adult mouse neural stem cells.

Example 14

In Vitro Proliferation Measured with ATP

Figure 3:
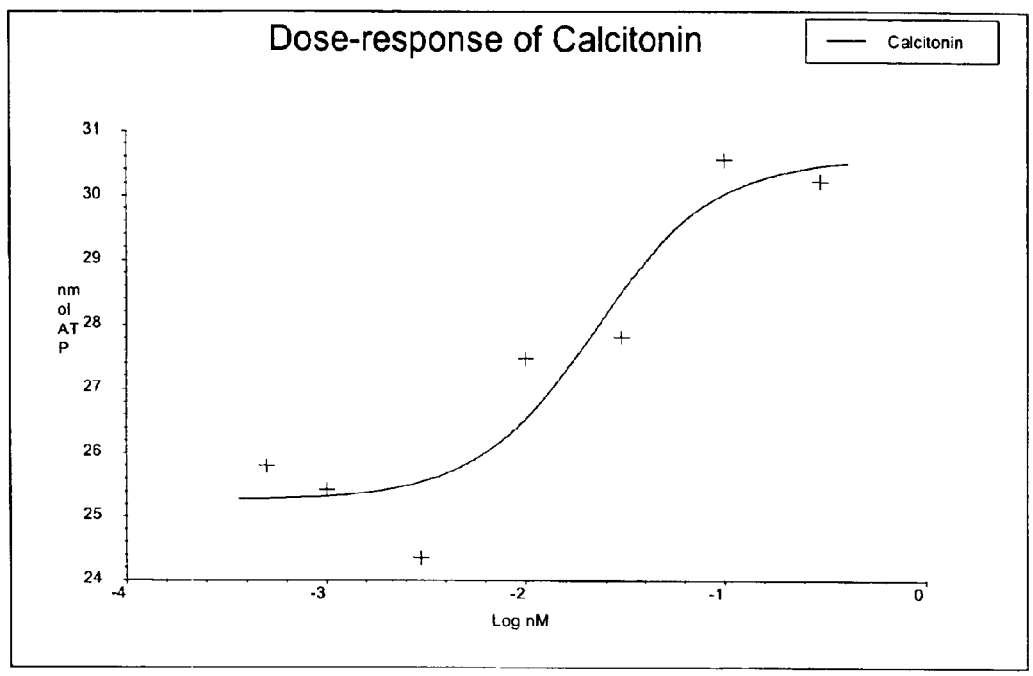
FIG. 3: is a dose response curve showing that the EC50 value for calcitonin is 0.03 nM.

In order to examine proliferative activity of exendin-4 and calcitonin we incubated neural stem cell cultures with either compound for 4 days. Unexpectedly, we found that both exendin-4 and calcitonin significantly increased ATP (proliferation) of neural stem cells as compared to vehicle treated controls. For exendin, the results show a ratio of 1.7-fold induction compared to control/non treated cells (p=0.049 student t-test; at 100 nM). At 10 M, calcitonin significantly increased the cell proliferation to 2.5-fold the level of control cells (p-value 0.027). The EC50 value for calcitonin is 0.03 nM as shown in the dose-response curve in FIG. 3.

Example 15

In Vivo Progenitor Cell Proliferation

Figure 2:
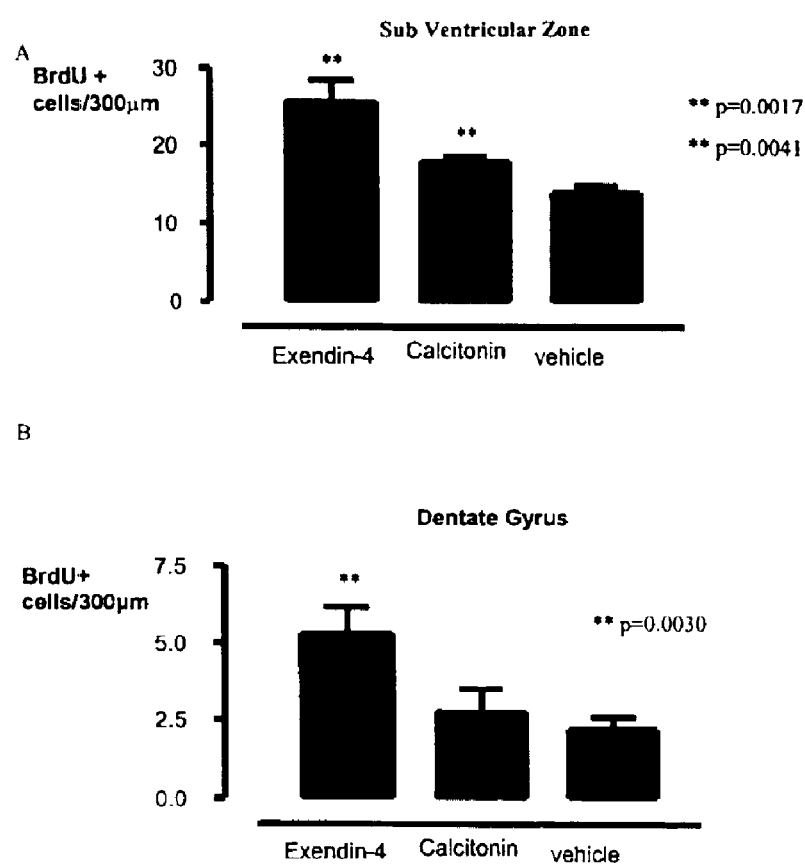
FIG. 2A and FIG. 2B: plots the number of BrdU positive cells after an animal is administered Exendin-4, calcitonin, or vehicle (sham injected with saline).

Two neurogenesis modulating agents, exendin-4 and calcitonin were separately administered intraperitoneally to Male Wistar rats weighing about 270 g (Harlan-Winkelmann Germany n=10) at various concentrations (1 $\mu$/kg and 10 mg/kg respectively in 0.1% RSA). The negative control (n=12), the vehicle group in FIG. 2, was injected with saline (in 0.1% RSA). Bromodeoxyuridine (BrdU; 50 mg/kg) was co-administrated together with the compounds. The intraperitoneally injections were given with a 12 hour interval for 7 days. Animals were perfused on day 8. The rats were kept at 12 hours light/dark regime. Feeding: included standard pellets, and feeding and drinking was ad libitum. Five animals were included in standard cage (Macrolon typeM4).

In perfusion, animals were perfused transcardially with 50 ml of ice cold phosphate buffered saline (PBS) and then 100 ml of 4% paraformaldehyde in PBS. Brains were fixed after removal in 4% paraformaldehyde in PBS for 24 hours at 4° C., at least 3 days before sectioning. Sections were prepared using a freezing microtome and stored in cyroprotectant at −20° C. before immunostaining for BrdU. Sections were immunostained for BrdU with mouse anti-BrdU paired with a biotinylated goat anti mouse IgG and visualized using ABC Elite kit (Vectorlabs. using manufactures directions). Standard light microscope techniques were used to count the total number of BrdU positive cells in each section and in relevant region of the brain. Analysis and quantification was performed for proliferative brain regions, subventricular zone, and the dentate gyros in hippocampus. Other experimental details not listed here are known to one of skill in the art and may be found for example in Pencea V et al. J. Neurosci Sep. 1 (2001). 21(17):6706–17.

Notably, we found that rats given intra-peritoneal infusion of exendin-4 or calcitonin co-administrated with BrdU twice daily showed a significant increase (nonparametric One-way ANOVA) in the number of newborn cells (BrdU positive compared to sham injected) in highly neurogenic regions including the sub ventricular zone and the dentate gyrus in the hippocampus (FIG. 2A and 2B). These data indicate that exendin-4 and calcitonin, in addition to previously described effects, also exhibit an unexpected neural stem cell proliferative effect pointing to neurogenesis.

Example 16

Progenitor Cell Proliferation

A neurogenesis modulating agent is administered intraperitoneally to adult test animals (n=12) at various concentrations from 0.01 to 100 mg/kg. Saline is given as a negative control. Starting two hours after neurogenesis modulating agent administration, animals are injected with four intraperitoneal injections of bromodeoxyuridine (BrdU; 50 mg/kg each) at three hour intervals. Animals are perfused after 1, 2, or 3 days or after 1, 2, 3, or 4 weeks after neurogenesis modulating agent administration. For animals studied for more than one day BrdU is administered by minipump.

In perfusion. animals are perfused transcardially with 50 ml of ice cold phosphate buffered saline (PBS) and then 100 ml of 4% paraformaldehyde in PBS. Brains are fixed after removal in 4% paraformaldehyde in PBS for 24 hours at 4 C for at least 3 days before sectioning. Sections are prepared using a freezing microtome and stored in cyroprotectant at −20 C before immunostaining for BrdU.

Sections are immunostained for BrdU with mouse anti-BrdU paired with a biotinylated goat anti-mouse IgG. Avidin-biotin-horseradish peroxidase (HRP) complex is applied to sections and immunoreactivity are visualized by reacting diaminobenzidine with the HRP. Standard techniques are used to estimate the total number of BrdU positive cells in each section and in each region of the brain.

Analysis and quantification is performed for proliferative brain regions, migratory streams, and areas of clinical relevance. Some, but not all. of these areas are exemplified below. This analysis is performed with DAB (diaminebenzidine) or fluorescence visualization using one or several of the following antibodies: as neuronal markers NeuN. Tuj1, anti-tyrosine hydroxylase, anti-MAP-2, etc.; as glial markers anti-GFAP, anti-S100, etc.; as oligodendrocyte markers anti-GalC, anti-PLP, etc. For BrdU visualization: anti-BrdU. Quantification is performed in all areas of the brain using stereological quantification. In particular, the following regions are of particular interest: dorsal hippocampus dentate gyrus, dorsal hippocampus CA1/alveus, olfactory bulb (OB), subventricular zone (SVZ), and striatum. Quantification of double-staining with confocal microscope is performed for every structure (e.g., OB, DG, CA1/alveus, SVZ, wall-to-striatum) checking BrdU+ for double-staining with the lineage markers. Other experimental details not listed here are known to one of skill in the art and may be found, for example, in Pencea V et al. J. Neurosci Sep. 1 (2001). 21(17):6706–17. The experiment is performed with wild type animals as well as an animal model of a neurological disease. Such models are enumerated in the detailed discussion section. One preferred animal is the mouse.

Other features of the invention will become apparent in the course of the following description of exemplary embodiments that are given for illustration of the invention and are not intended to be limiting thereof. Throughout this specification, various patents, published applications, GenBank DNA and protein sequences, and scientific references are cited to describe the state and content of the art. Those disclosures, in their entireties, are hereby incorporated into the present specification by reference.

References

Biebl M. Cooper C M. Winkler J. Kuhn H G (2000) Analysis of neurogenesis and programmed cell death reveals a self-renewing capacity in the adult rat brain. Neurosci Lett 291:17–20.

Craig C G. Tropepe V. Morshead C M. Reynolds B A. Weiss S. van der Kooy D (1996) In vivo growth factor expansion of endogenous subependymal neural precursor cell populations in the adult mouse brain. J Neurosci 16:2649–2658.

Doetsch F. Caille I. Lim D A. Garcia-Verdugo J M. Alvarez-Buylla A (1999) Subventricular zone astrocytes are neural stem cells in the adult mammalian brain. Cell 97:703–716.

Gage F H. Kempermann G. Palmer T D. Peterson D A. Ray J (1998) Multipotent progenitor cells in the adult dentate gyrus. J Neurobiol 36:249–266.

Herman J P. Abrous N D (1994) Dopaminergic neural grafts after fifteen years: results and perspectives. Prog Neurobiol 44:1–35.

Jacobson M (1991) Histosenesis and morphogenesis of cortical structures. In: Developmental Neurobiology. pp 401–451: Plenum Press. New York.

Johansson C B. Svensson M. Wallstedt L. Janson A M. Frisen J (1999a) Neural stem cells in the adult human brain. Exp Cell Res 253:733–736.

Johansson C B. Momma S. Clarke D L. Risling M. Lendahl U. Frisen J (1999b) Identification of a neural stem cell in the adult mammalian central nervous system. Cell 96:25–34.

Johe K K. Hazel T G. Muller T. Dugich-Djordjevic M M. McKay R D (1996) Single factors direct the differentiation of stem cells from the fetal and adult central nervous system. Genes Dev 10:3129–3140.

Kuhn H G. Winkler J. Kempermann G. Thal L J. Gage F H (1997) Epidermal growth factor and fibroblast growth factor-2 have different effects on neural progenitors in the adult rat brain. J Neurosci 17:5820–5829.

Lois C. Alvarez-Buylla A (1993) Proliferating subventricular zone cells in the adult mammalian forebrain can differentiate into neurons and glia. Proc Natl Acad Sci USA 90:2074–2077.

Lonze B E. Ginty D D (2002) Function and regulation of CREB family transcription factors in the nervous system. Neuron 35:605–623.

Magavi S S. Leavitt B R. Macklis J D (2000) Induction of neurogenesis in the neocortex of adult mice [see comments]. Nature 405:951–955.

McKay R (1997) Stem cells in the central nervous system. Science 276:66–71.

Nakatomi H. Kuriu T. Okabe S. Yamamoto S. Hatano O. Kawahara N. Tamura A. Kirino T. Nakafuku M (2002) Regeneration of hippocampal pyramidal neurons after ischemic brain injury by recruitment of endogenous neural progenitors. Cell 110:429441.

Neves S R. Ram P T. Iyengar R (2002) G protein pathways. Science 296:1636–1639.

Palmer T D. Markakis E A. Willhoite A R. Safar F. Gage F H (1999) Fibroblast growth factor-2 activates a latent neurogenic program in neural stem cells from diverse regions of the adult CNS. J Neurosci 19:8487–8497.

Patrone C. Andersson S. Korhonen L. Lindholm D (1999) Estrogen receptor-dependent regulation of sensory neuron survival in developing dorsal root ganglion. Proc Natl Acad Sci USA 96:10905–10910.

Pencea V. Bingaman K D. Wiegand S J. Luskin M B (2001) Infusion of Brain-Derived Neurotrophic Factor into the Lateral Ventricle of the Adult Rat Leads to New Neurons in the Parenchyma of the Striatum. Septum. Thalamus. and Hypothalamus. J Neurosci 21:6706–6717.

Rajan P. McKay R D (1998) Multiple routes to astrocytic differentiation in the CNS. J Neurosci 18:3620–3629.

Rao A. Luo C. Hogan P G (1997) Transcription factors of the NFAT family: regulation and function. Annu Rev Immunol 15:707–747.

Snyder E Y. Yoon C. Flax J D. Macklis J D (1997) Multipotent neural precursors can differentiate toward replacement of neurons undergoing targeted apoptotic degeneration in adult mouse neocortex. Proc Natl Acad Sci USA 94:11663–11668.

Williams B P. Park J K. Alberta J A. Muhlebach S G. Hwang G Y. Roberts T M. Stiles C D (1997) A PDGF-regulated immediate early gene response initiates neuronal differentiation in ventricular zone progenitor cells. Neuron 18:553–562.

Zhao M. Momma S. Delfani K. Carlen M. Cassidy R M. Johansson C B. Brismar H. Shupliakov O. Frisen J. Janson A M (2003) Evidence for neurogenesis in the adult mammalian substantia nigra. Proc Natl Acad Sci USA 100:7925–7930.

---

What is claimed is:

1. A method for increasing neurogenesis in neural tissue of a patient exhibiting at least one symptom of a central nervous system disorder selected from the group consisting of neurodegenerative disorders, ischemic disorders, neurological traumas, and learning and memory disorders, comprising:

administrating at least one agent selected from the group consisting of calcitonin, exendin and their analogs that elevate intracellular cAMP levels in the tissue, wherein the agent increases neurogenesis in the patient, thereby increasing neurogenesis in the neural tissue of the patient.

2. The method of claim 1 wherein said agent is a neurogenesis increasing agent selected from the group consisting of thyrocalcitonin, calcitonin, exendin-3, exendin-4, and analogs and combinations thereof.

3. The method of claim 2 wherein said agent is an calcitonin analog selected from the group consisting of katacalcin, calcitonin-gene-related-peptide, calcitonin-receptor-stimulating-peptides 1, calcitonin-receptor-stimulating-peptides 2, calcitonin-receptor-stimulating-peptides 3, histidine-methionine amide peptide hormone (PHM-27), Intermedin, side-chain bridged salmon calcitonin (Asp(17), Lys(21)), side-chain bridged salmon calcitonin (Asp(17) Orn(21)), a peptide comprising an amino acid sequence of SEQ ID NO:17 (AC512) benzophenone-containing calcitonin analogs, salmon calcitonin analog (Arg(11,18), Lys(14)), eel calcitonin analog, calcitonin 8–32, and analogs and combinations thereof.

4. The method of claim 2 wherein said agent is a calcitonin analog selected from the group consisting of calcitonin gene related peptide 8–37 (CGRP 8–37), amylin amide, and analogs thereof.

5. The method of claim 2 wherein said agent is an exendin analog selected from the group consisting of glucagon-like peptide-1 (GLP 1 peptide), glucagon-like peptide-1 analog, a polypeptide comprising an amino acid sequence of $HA_8EGTFTSDVSSYLEGQAAKEF\ IAWLVKGRK_{37}$ wherein $A_8$ is a D-Ala and wherein a [2-[2-[2-maleimidopropionamido(ethoxy)ethoxy] acetamide is attached to the epsilon amino group of $K_{37}$ (CJC-1131), liraglutide, pramlintide, AVE-0010, (Ser2)-exendin (1–9), and alpha-me-glucagon-like peptide-1 (alpha-me-GLP-1).

6. The method of claim 1 wherein the agent is a glucagon-like peptide-1 (GIP-1) receptor ligand peptide or pituitary adenylate cyclase activating (PACAP) receptor ligand peptide.

7. The method of claim 1 wherein the nervous system disorder is selected from the group consisting of Parkinson's disease and Parkinsonian disorders, Huntington's disease, Alzheimers disease, multiple sclerosis, amyotrophic lateral sclerosis, Shy-prager syndrome, progressive supranuclear palsy, Lewy body disease, spinal ischemia, ischemic stroke, cerebral infarction, spinal cord injury, and cancer-related brain and spinal cord injury, multi-infarct dementia, geriatric dementia, cognition impairment and depression.

8. The method of claim 1 wherein increasing neurogenesis is modulating proliferation, differentiation, migration, or survival of a neural stem cells or progenitor cells in said neural tissue.

9. The method of claim 1 wherein said agent elevates the intracellular cAMP levels of said tissue above 20% as compared to a tissue not administered said agent.

10. The method of claim 1 wherein the agent is administered to the central nervous system of the patient.

11. The method of claim 1 wherein the agent is administered by a route selected from the group consisting of oral, subcutaneous, intraperitoneal, intramuscular, intracerebroventricular, intraparenchymal, intrathecal, intracranial, buccal, mucosal, nasal, and rectal administration.

12. The method of claim 1 wherein the agent is administered by a liposome delivery system.

13. The method of claim 1 wherein said increasing neurogenesis comprise maintaining or increasing the amount or percentage of doublecortin positive cells in the neural tissue relative to a patient not administered said agent.

14. The method of claim 1 wherein said increasing neurogenesis is performed by an activation of a G-protein coupled receptor (GPCR) in said neural tissue.

15. The method of claim 1 wherein the agent is administered to achieve a tissue concentration of 0.0001 nM to 50 nM.

16. A method for increasing neurogenesis in neural tissue of a patient exhibiting at least one symptom of a central nervous system disorder selected from the group consisting of neurodegenerative disorders, ischemic disorders, neurological traumas, and learning and memory disorders, comprising:

administrating at least one agent selected from the group consisting of thyrocalcitonin, calcitonin, exendin-3, exendin-4, and analogs and combinations thereof wherein the agent increases neurogenesis in the patient, thereby increasing neurogenesis in the neural tissue of the patient.

* * * * *